(12) United States Patent
Zeng et al.

(10) Patent No.: US 10,765,789 B2
(45) Date of Patent: Sep. 8, 2020

(54) IMPELLER FOR CATHETER PUMP

(71) Applicant: TC1 LLC, St. Paul, MN (US)

(72) Inventors: Zijing Zeng, Sunnyvale, CA (US);
Phyllis Yuen, Fremont, CA (US);
Michael R. Butler, Dublin, CA (US)

(73) Assignee: TC1 LLC, St. Paul, MN (US)

( * ) Notice: Subject to any disclaimer, the term of this patent is extended or adjusted under 35 U.S.C. 154(b) by 126 days.

(21) Appl. No.: 16/026,995

(22) Filed: Jul. 3, 2018

(65) Prior Publication Data

US 2018/0311423 A1 Nov. 1, 2018

Related U.S. Application Data

(63) Continuation of application No. 15/589,366, filed on May 8, 2017, now Pat. No. 10,039,872, which is a
(Continued)

(51) Int. Cl.
*A61M 1/10* (2006.01)
*A61M 1/12* (2006.01)
*F04D 29/18* (2006.01)

(52) U.S. Cl.
CPC .......... *A61M 1/1029* (2014.02); *A61M 1/101* (2013.01); *A61M 1/1024* (2014.02);
(Continued)

(58) Field of Classification Search
CPC .... A61M 1/001; A61M 1/1024; A61M 1/122; A61M 1/1029; A61M 1/1034; A61M 1/125; A61M 1/1086; A61M 1/1012; A61M 2205/3334; F04D 29/183; F04C 2270/0421

See application file for complete search history.

(56) References Cited

U.S. PATENT DOCUMENTS 1,002,833 A * 9/1911 Giddings .................. F03D 1/04
415/4.4
1,031,629 A * 7/1912 De Los Rios ................ 416/176
(Continued)

FOREIGN PATENT DOCUMENTS

CA 2701810 A1 4/2009
EP 0453234 A1 10/1991
(Continued)

OTHER PUBLICATIONS

Schmitz-Rode et al., "Axial flow catheter pump for circulatory support," Biomedizinische Technik, 2002, Band 4 7, Erganzungsband 1, Tei I 1, pp. 142-143.
(Continued)

*Primary Examiner* — Igor Kershteyn
(74) *Attorney, Agent, or Firm* — Armstrong Teasdale LLP

(57) ABSTRACT

An impeller for a pump is disclosed herein. The impeller can include a hub having a fixed end and a free end. The impeller can also have a plurality of blades supported by the hub. Each blade can have a fixed end coupled to the hub and a free end. The impeller can have a stored configuration and a deployed configuration, the blades in the deployed configuration extending away from the hub, and the blades in the stored configuration being compressed against the hub.

19 Claims, 20 Drawing Sheets

Related U.S. Application Data continuation of application No. 15/142,522, filed on Apr. 29, 2016, now Pat. No. 9,675,740, which is a continuation of application No. 14/401,096, filed as application No. PCT/US2013/040809 on May 13, 2013, now Pat. No. 9,327,067, which is a continuation of application No. 13/802,570, filed on Mar. 13, 2013, now Pat. No. 8,721,517.

(60) Provisional application No. 61/667,875, filed on Jul. 3, 2012, provisional application No. 61/646,827, filed on May 14, 2012.

(52) U.S. Cl.
CPC .......... *A61M 1/122* (2014.02); *F04D 29/183* (2013.01); *A61M 1/1012* (2014.02); *A61M 1/1034* (2014.02); *A61M 1/1086* (2013.01); *A61M 1/125* (2014.02); *A61M 2205/3334* (2013.01); *F04C 2270/0421* (2013.01)

(56) References Cited

U.S. PATENT DOCUMENTS

| | | |
|---|---|---|
| 1,814,175 A * | 7/1931 | Miller .................. B63H 5/14 415/74 |
| 1,902,418 A | 3/1933 | Pilgrim |
| 2,356,659 A | 8/1944 | Paiva |
| 2,649,052 A | 8/1953 | Weyer |
| 2,664,050 A | 12/1953 | Abresch |
| 2,684,035 A | 7/1954 | Kemp |
| 2,789,511 A | 4/1957 | Warren |
| 2,896,926 A | 7/1959 | Chapman |
| 2,935,068 A | 5/1960 | Shearman |
| 3,080,824 A | 3/1963 | Boyd |
| 3,455,540 A | 7/1969 | Marcmann |
| 3,510,229 A | 5/1970 | Smith |
| 3,812,812 A | 5/1974 | Hurwitz |
| 3,860,968 A | 1/1975 | Shapiro |
| 3,904,901 A | 9/1975 | Renard et al. |
| 3,995,617 A | 12/1976 | Watkins et al. |
| 4,115,040 A | 9/1978 | Knorr |
| 4,129,129 A | 12/1978 | Amrine |
| 4,135,253 A | 1/1979 | Reich et al. |
| 4,143,425 A | 3/1979 | Runge |
| 4,149,535 A | 4/1979 | Volder |
| 4,304,524 A | 12/1981 | Coxon |
| D264,134 S | 4/1982 | Xanthopoulos |
| 4,382,199 A | 5/1983 | Isaacson |
| 4,392,836 A | 7/1983 | Sugawara |
| 4,458,366 A | 7/1984 | MacGregor et al. |
| 4,537,561 A | 8/1985 | Xanthopoulos |
| 4,540,402 A | 9/1985 | Aigner |
| 4,560,375 A | 12/1985 | Schulte et al. |
| 4,589,822 A | 5/1986 | Clausen et al. |
| 4,625,712 A | 12/1986 | Wampler |
| 4,655,745 A | 4/1987 | Corbett et al. |
| 4,673,334 A | 6/1987 | Allington et al. |
| 4,686,982 A | 8/1987 | Nash |
| 4,696,667 A | 9/1987 | Masch |
| 4,704,121 A | 11/1987 | Moise |
| 4,728,319 A | 3/1988 | Masch et al. |
| 4,753,221 A | 6/1988 | Kensey et al. |
| 4,769,006 A | 9/1988 | Papantonakos |
| 4,817,586 A | 4/1989 | Wampler |
| 4,846,152 A * | 7/1989 | Wampler .................. F04D 1/04 600/16 |
| 4,895,557 A | 1/1990 | Moise et al. |
| 4,900,227 A | 2/1990 | Trouplin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,944,722 A | 7/1990 | Carriker et al. |
| 4,955,856 A | 9/1990 | Phillips |
| 4,957,504 A | 9/1990 | Chardack |
| 4,964,864 A | 10/1990 | Summers et al. |
| 4,969,865 A | 11/1990 | Hwang et al. |
| 4,976,270 A | 12/1990 | Parl et al. |
| 4,985,014 A | 1/1991 | Orejola |
| 4,994,017 A | 2/1991 | Yozu |
| 4,995,857 A | 2/1991 | Arnold |
| 5,000,177 A | 3/1991 | Hoffmann et al. |
| 5,021,048 A | 6/1991 | Buckholtz |
| 5,044,902 A | 9/1991 | Malbec |
| 5,045,072 A | 9/1991 | Castillo et al. |
| 5,049,134 A | 9/1991 | Golding |
| 5,059,174 A | 10/1991 | Vaillancourt |
| 5,061,256 A | 10/1991 | Wampler |
| 5,089,016 A | 2/1992 | Millner et al. |
| 5,092,844 A | 3/1992 | Schwartz et al. |
| 5,098,256 A | 3/1992 | Smith |
| 5,106,368 A | 4/1992 | Uldall et al. |
| 5,112,200 A | 5/1992 | Isaacson et al. |
| 5,112,292 A | 5/1992 | Hwang et al. |
| 5,112,349 A | 5/1992 | Summers et al. |
| 5,129,883 A | 7/1992 | Black |
| 5,142,155 A | 8/1992 | Mauze et al. |
| 5,147,186 A | 9/1992 | Buckholtz |
| 5,163,910 A | 11/1992 | Schwartz et al. |
| 5,169,378 A | 12/1992 | Figuera |
| 5,171,212 A | 12/1992 | Buck et al. |
| 5,190,528 A | 3/1993 | Fonger et al. |
| 5,195,960 A | 3/1993 | Hossain et al. |
| 5,201,679 A | 4/1993 | Velte, Jr. et al. |
| 5,211,546 A | 5/1993 | Isaacson et al. |
| 5,221,270 A | 6/1993 | Parker |
| 5,234,407 A | 8/1993 | Teirstein et al. |
| 5,234,416 A | 8/1993 | Macaulay et al. |
| 5,290,227 A | 3/1994 | Pasque |
| 5,300,112 A | 4/1994 | Barr |
| 5,312,341 A | 5/1994 | Turi |
| 5,344,443 A | 9/1994 | Palma et al. |
| 5,346,458 A | 9/1994 | Affeld |
| 5,360,317 A | 11/1994 | Clausen et al. |
| 5,376,114 A | 12/1994 | Jarvik |
| 5,393,197 A | 2/1995 | Lemont et al. |
| 5,393,207 A | 2/1995 | Maher |
| 5,405,341 A | 4/1995 | Martin |
| 5,405,383 A | 4/1995 | Barr |
| 5,415,637 A | 5/1995 | Khosravi |
| 5,437,541 A | 8/1995 | Vainrub |
| 5,449,342 A | 9/1995 | Hirose et al. |
| 5,458,459 A | 10/1995 | Hubbard et al. |
| 5,490,763 A | 2/1996 | Abrams et al. |
| 5,505,701 A | 4/1996 | Anaya Fernandez de Lomana et al. |
| 5,527,159 A * | 6/1996 | Bozeman, Jr. .......... A61M 1/10 417/45 |
| 5,533,957 A | 7/1996 | Aldea |
| 5,534,287 A | 7/1996 | Lukic |
| 5,554,114 A | 9/1996 | Wallace et al. |
| 5,586,868 A | 12/1996 | Lawless et al. |
| 5,588,812 A | 12/1996 | Taylor et al. |
| 5,609,574 A | 3/1997 | Kaplan et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,692,882 A * | 12/1997 | Bozeman, Jr. .......... A61M 1/10 417/45 |
| 5,702,418 A | 12/1997 | Ravenscroft |
| 5,704,926 A | 1/1998 | Sutton |
| 5,707,218 A | 1/1998 | Maher et al. |
| 5,722,930 A | 3/1998 | Larson, Jr. et al. |
| 5,725,513 A | 3/1998 | Ju et al. |
| 5,725,570 A | 3/1998 | Heath |
| 5,730,628 A | 3/1998 | Hawkins |
| 5,735,897 A | 4/1998 | Buirge |
| 5,738,649 A | 4/1998 | Macoviak |
| 5,741,234 A | 4/1998 | Aboul-Hosn |
| 5,741,429 A | 4/1998 | Donadio et al. |
| 5,746,709 A | 5/1998 | Rom et al. |
| 5,749,855 A | 5/1998 | Reitan |

(56) References Cited

U.S. PATENT DOCUMENTS

| | | |
|---|---|---|
| 5,755,784 A | 5/1998 | Jarvik |
| 5,776,111 A | 7/1998 | Tesio |
| 5,776,161 A | 7/1998 | Globerman |
| 5,776,190 A | 7/1998 | Jarvik |
| 5,779,721 A | 7/1998 | Nash |
| 5,807,311 A | 9/1998 | Palestrant |
| 5,814,011 A | 9/1998 | Corace |
| 5,824,070 A | 10/1998 | Jarvik |
| 5,851,174 A | 12/1998 | Jarvik et al. |
| 5,859,482 A | 1/1999 | Crowell et al. |
| 5,868,702 A | 2/1999 | Stevens et al. |
| 5,868,703 A | 2/1999 | Bertolero et al. |
| 5,888,241 A | 3/1999 | Jarvik |
| 5,888,242 A | 3/1999 | Antaki et al. |
| 5,911,685 A | 6/1999 | Siess et al. |
| 5,921,913 A | 7/1999 | Siess |
| 5,927,956 A | 7/1999 | Lim et al. |
| 5,941,813 A | 8/1999 | Sievers et al. |
| 5,951,263 A | 9/1999 | Taylor et al. |
| 5,957,941 A | 9/1999 | Ream |
| 5,964,694 A | 10/1999 | Siess et al. |
| 5,993,420 A | 11/1999 | Hyman et al. |
| 6,007,478 A | 12/1999 | Siess et al. |
| 6,007,479 A | 12/1999 | Rottenberg et al. |
| 6,015,272 A | 1/2000 | Antaki et al. |
| 6,015,434 A | 1/2000 | Yamane |
| 6,018,208 A | 1/2000 | Maher et al. |
| 6,027,863 A | 2/2000 | Donadio |
| 6,053,705 A | 4/2000 | Schoeb et al. |
| 6,056,719 A | 5/2000 | Mickley |
| 6,058,593 A | 5/2000 | Siess |
| 6,059,760 A | 5/2000 | Sandmore et al. |
| 6,068,610 A | 5/2000 | Ellis et al. |
| 6,071,093 A | 6/2000 | Hart |
| 6,083,260 A | 7/2000 | Aboul-Hosn |
| 6,086,527 A | 7/2000 | Talpade |
| 6,086,570 A | 7/2000 | Aboul-Hosn et al. |
| 6,106,494 A | 8/2000 | Saravia et al. |
| 6,109,895 A | 8/2000 | Ray et al. |
| 6,113,536 A | 9/2000 | Aboul-Hosn et al. |
| 6,123,659 A | 9/2000 | Le Blanc et al. |
| 6,123,725 A | 9/2000 | Aboul-Hosn |
| 6,132,363 A | 10/2000 | Freed et al. |
| 6,135,729 A * | 10/2000 | Aber ............... A61M 1/10 417/356 |
| 6,135,943 A | 10/2000 | Yu et al. |
| 6,136,025 A | 10/2000 | Barbut et al. |
| 6,139,487 A | 10/2000 | Siess |
| 6,152,704 A | 11/2000 | Aboul-Hosn et al. |
| 6,162,194 A | 12/2000 | Shipp |
| 6,176,822 B1 | 1/2001 | Nix et al. |
| 6,176,848 B1 | 1/2001 | Rau et al. |
| 6,178,922 B1 | 1/2001 | Denesuk et al. |
| 6,186,665 B1 | 2/2001 | Maher et al. |
| 6,190,304 B1 | 2/2001 | Downey et al. |
| 6,190,357 B1 | 2/2001 | Ferrari et al. |
| 6,200,260 B1 | 3/2001 | Bolling |
| 6,203,528 B1 | 3/2001 | Deckert et al. |
| 6,210,133 B1 | 4/2001 | Aboul-Hosn et al. |
| 6,210,318 B1 | 4/2001 | Lederman |
| 6,210,397 B1 | 4/2001 | Aboul-Hosn et al. |
| 6,214,846 B1 | 4/2001 | Elliott |
| 6,217,541 B1 | 4/2001 | Yu |
| 6,227,797 B1 | 5/2001 | Watterson et al. |
| 6,228,063 B1 | 5/2001 | Aboul Hosn |
| 6,234,960 B1 | 5/2001 | Aboul-Hosn et al. |
| 6,234,995 B1 | 5/2001 | Peacock, III |
| 6,245,007 B1 | 6/2001 | Bedingham et al. |
| 6,245,026 B1 | 6/2001 | Campbell et al. |
| 6,247,892 B1 | 6/2001 | Kazatchkov et al. |
| 6,248,091 B1 | 6/2001 | Voelker |
| 6,254,359 B1 | 7/2001 | Aber |
| 6,254,564 B1 | 7/2001 | Wilk et al. |
| 6,287,319 B1 | 9/2001 | Aboul-Hosn et al. |
| 6,287,336 B1 | 9/2001 | Globerman et al. |
| 6,295,877 B1 | 10/2001 | Aboul-Hosn et al. |
| 6,299,635 B1 | 10/2001 | Frantzen |
| 6,305,962 B1 | 10/2001 | Maher et al. |
| 6,387,037 B1 | 5/2002 | Bolling et al. |
| 6,395,026 B1 | 5/2002 | Aboul-Hosn et al. |
| 6,413,222 B1 | 7/2002 | Pantages et al. |
| 6,422,990 B1 | 7/2002 | Prem |
| 6,425,007 B1 | 7/2002 | Messinger |
| 6,428,464 B1 | 8/2002 | Bolling |
| 6,447,441 B1 | 9/2002 | Yu et al. |
| 6,454,775 B1 | 9/2002 | Demarais et al. |
| 6,468,298 B1 | 10/2002 | Pelton |
| 6,494,694 B2 | 12/2002 | Lawless et al. |
| 6,503,224 B1 | 1/2003 | Forman et al. |
| 6,508,777 B1 | 1/2003 | MacOviak et al. |
| 6,508,787 B2 | 1/2003 | Erbel et al. |
| 6,517,315 B2 | 2/2003 | Belady |
| 6,517,528 B1 | 2/2003 | Pantages et al. |
| 6,527,699 B1 | 3/2003 | Goldowsky |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | DeBlanc et al. |
| 6,565,598 B1 | 5/2003 | Lootz |
| 6,572,349 B2 | 6/2003 | Sorensen et al. |
| 6,609,883 B2 | 8/2003 | Woodard et al. |
| 6,610,004 B2 | 8/2003 | Viole et al. |
| 6,613,008 B2 | 9/2003 | Aboul-Hosn et al. |
| 6,616,323 B2 | 9/2003 | McGill |
| 6,623,420 B2 | 9/2003 | Reich et al. |
| 6,623,475 B1 | 9/2003 | Siess |
| 6,641,093 B2 | 11/2003 | Coudrais |
| 6,641,558 B1 | 11/2003 | Aboul-Hosn et al. |
| 6,645,241 B1 | 11/2003 | Strecker |
| 6,652,548 B2 | 11/2003 | Evans et al. |
| 6,660,014 B2 | 12/2003 | Demarais et al. |
| 6,673,105 B1 | 1/2004 | Chen |
| 6,692,318 B2 | 2/2004 | McBride |
| 6,709,418 B1 | 3/2004 | Aboul-Hosn et al. |
| 6,716,189 B1 | 4/2004 | Jarvik et al. |
| 6,749,598 B1 | 6/2004 | Keren et al. |
| 6,776,578 B2 | 8/2004 | Belady |
| 6,776,794 B1 | 8/2004 | Hong et al. |
| 6,783,328 B2 | 8/2004 | Lucke et al. |
| 6,790,171 B1 | 9/2004 | Gruendeman et al. |
| 6,794,784 B2 | 9/2004 | Takahashi et al. |
| 6,794,789 B2 | 9/2004 | Siess et al. |
| 6,814,713 B2 | 11/2004 | Aboul Hosn et al. |
| 6,817,836 B2 | 11/2004 | Nose et al. |
| 6,818,001 B2 | 11/2004 | Wulfman et al. |
| 6,835,049 B2 | 12/2004 | Ray |
| 6,860,713 B2 | 3/2005 | Hoover |
| 6,866,625 B1 | 3/2005 | Ayre et al. |
| 6,866,805 B2 | 3/2005 | Hong et al. |
| 6,887,215 B2 | 5/2005 | McWeeney |
| 6,889,082 B2 | 5/2005 | Bolling et al. |
| 6,901,289 B2 | 5/2005 | Dahl et al. |
| 6,926,662 B1 | 8/2005 | Aboul-Hosn et al. |
| 6,935,344 B1 | 8/2005 | Aboul-Hosn et al. |
| 6,942,611 B2 | 9/2005 | Siess |
| 6,949,066 B2 | 9/2005 | Bearnson et al. |
| 6,962,488 B2 | 11/2005 | Davis et al. |
| 6,966,748 B2 | 11/2005 | Woodard et al. |
| 6,972,956 B2 | 12/2005 | Franz et al. |
| 6,974,436 B1 | 12/2005 | Aboul-Hosn et al. |
| 6,981,942 B2 | 1/2006 | Khaw et al. |
| 6,984,392 B2 | 1/2006 | Bechert et al. |
| 7,010,954 B2 | 3/2006 | Siess et al. |
| 7,011,620 B1 | 3/2006 | Siess |
| 7,014,417 B2 | 3/2006 | Salomon |
| 7,018,182 B2 | 3/2006 | O'Mahony et al. |
| 7,022,100 B2 | 4/2006 | Aboul-Hosn et al. |
| 7,027,875 B2 | 4/2006 | Siess et al. |
| 7,037,069 B2 | 5/2006 | Arnold et al. |
| 7,070,555 B2 | 7/2006 | Siess |
| 7,122,019 B1 | 10/2006 | Kesten et al. |
| 7,125,376 B2 | 10/2006 | Viole et al. |
| 7,144,365 B2 | 12/2006 | Bolling et al. |
| 7,150,711 B2 | 12/2006 | Nusser et al. |

(56) References Cited

U.S. PATENT DOCUMENTS

| | | | |
|---|---|---|---|
| 7,160,243 B2 | 1/2007 | Medvedev |
| 7,172,551 B2 | 2/2007 | Leasure |
| 7,175,588 B2 | 2/2007 | Morello |
| 7,214,038 B2 | 5/2007 | Saxer et al. |
| 7,229,258 B2 | 6/2007 | Wood et al. |
| 7,238,010 B2 | 7/2007 | Hershberger et al. |
| 7,241,257 B1 | 7/2007 | Ainsworth et al. |
| 7,262,531 B2 | 8/2007 | Li et al. |
| 7,264,606 B2 | 9/2007 | Jarvik et al. |
| 7,267,667 B2 | 9/2007 | Houde et al. |
| 7,284,956 B2 | 10/2007 | Nose et al. |
| 7,284,958 B2 | 10/2007 | Dundas et al. |
| 7,288,111 B1 | 10/2007 | Holloway et al. |
| 7,290,929 B2 | 11/2007 | Smith et al. |
| 7,329,236 B2 | 2/2008 | Kesten et al. |
| 7,331,921 B2 | 2/2008 | Viole et al. |
| 7,335,192 B2 | 2/2008 | Keren et al. |
| 7,341,570 B2 | 3/2008 | Keren et al. |
| 7,381,179 B2 | 6/2008 | Aboul-Hosn et al. |
| 7,393,181 B2 | 7/2008 | McBride et al. |
| 7,455,497 B2 * | 11/2008 | Lee ................ F04D 13/10 |
| | | | 415/72 |
| 7,469,716 B2 | 12/2008 | Parrino et al. |
| 7,478,999 B2 | 1/2009 | Limoges |
| 7,491,163 B2 | 2/2009 | Viole et al. |
| 7,534,258 B2 | 5/2009 | Gomez et al. |
| 7,605,298 B2 | 10/2009 | Bechert et al. |
| 7,619,560 B2 | 11/2009 | Penna et al. |
| 7,633,193 B2 | 12/2009 | Masoudipour et al. |
| 7,645,225 B2 | 1/2010 | Medvedev et al. |
| 7,657,324 B2 | 2/2010 | Westlund et al. |
| 7,682,673 B2 | 3/2010 | Houston et al. |
| 7,722,568 B2 | 5/2010 | Lenker et al. |
| 7,731,675 B2 | 6/2010 | Aboul-Hosn et al. |
| 7,736,296 B2 | 6/2010 | Siess et al. |
| 7,758,521 B2 | 7/2010 | Morris et al. |
| 7,766,892 B2 | 8/2010 | Keren et al. |
| 7,780,628 B1 | 8/2010 | Keren et al. |
| 7,785,246 B2 | 8/2010 | Aboul-Hosn et al. |
| 7,811,279 B2 | 10/2010 | John |
| 7,819,833 B2 | 10/2010 | Ainsworth et al. |
| 7,820,205 B2 | 10/2010 | Takakusagi et al. |
| 7,828,710 B2 | 11/2010 | Shifflette |
| 7,841,976 B2 | 11/2010 | McBride et al. |
| 7,878,967 B1 | 2/2011 | Khanal |
| 7,918,828 B2 | 4/2011 | Lundgaard et al. |
| 7,927,068 B2 | 4/2011 | McBride et al. |
| 7,934,912 B2 | 5/2011 | Voltenburg, Jr. et al. |
| 7,935,102 B2 | 5/2011 | Breznock et al. |
| 7,942,804 B2 | 5/2011 | Khaw |
| 7,942,844 B2 | 5/2011 | Moberg et al. |
| 7,955,365 B2 | 6/2011 | Doty |
| 7,993,259 B2 | 8/2011 | Kang et al. |
| 7,998,054 B2 | 8/2011 | Bolling |
| 7,998,190 B2 | 8/2011 | Gharib et al. |
| 8,012,079 B2 | 9/2011 | Delgado |
| 8,025,647 B2 | 9/2011 | Siess et al. |
| 8,052,399 B2 | 11/2011 | Stemple et al. |
| 8,062,008 B2 | 11/2011 | Voltenburg, Jr. et al. |
| 8,079,948 B2 | 12/2011 | Shifflette |
| 8,110,267 B2 | 2/2012 | Houston et al. |
| 8,114,008 B2 | 2/2012 | Hidaka et al. |
| 8,123,669 B2 | 2/2012 | Siess et al. |
| 8,142,400 B2 | 3/2012 | Rotem et al. |
| 8,177,703 B2 | 5/2012 | Smith et al. |
| 8,206,350 B2 | 6/2012 | Mann et al. |
| 8,209,015 B2 | 6/2012 | Glenn |
| 8,216,122 B2 | 7/2012 | Kung et al. |
| 8,235,943 B2 | 8/2012 | Breznock et al. |
| 8,236,040 B2 | 8/2012 | Mayberry et al. |
| 8,236,044 B2 | 8/2012 | Robaina |
| 8,255,050 B2 | 8/2012 | Mohl |
| 8,257,312 B2 | 9/2012 | Duffy |
| 8,262,619 B2 | 9/2012 | Chebator et al. |
| 8,277,470 B2 | 10/2012 | Demarais et al. |
| 8,317,715 B2 | 11/2012 | Belleville et al. |
| 8,329,913 B2 | 12/2012 | Murata et al. |
| 8,333,687 B2 | 12/2012 | Farnan et al. |
| 8,348,991 B2 | 1/2013 | Weber et al. |
| 8,364,278 B2 | 1/2013 | Pianca et al. |
| 8,376,707 B2 | 2/2013 | McBride et al. |
| 8,382,818 B2 | 2/2013 | Davis et al. |
| 8,388,565 B2 | 3/2013 | Shifflette |
| 8,409,128 B2 | 4/2013 | Ferrari |
| 8,414,645 B2 | 4/2013 | Dwork et al. |
| 8,439,859 B2 * | 5/2013 | Pfeffer ................ A61M 1/12 |
| | | | 604/6.11 |
| 8,449,443 B2 | 5/2013 | Rodefeld et al. |
| 8,485,961 B2 | 7/2013 | Campbell et al. |
| 8,489,190 B2 | 7/2013 | Pfeffer et al. |
| 8,535,211 B2 | 9/2013 | Campbell et al. |
| 8,540,615 B2 | 9/2013 | Aboul-Hosn et al. |
| 8,545,379 B2 | 10/2013 | Marseille et al. |
| 8,545,380 B2 | 10/2013 | Farnan et al. |
| 8,579,858 B2 | 11/2013 | Reitan et al. |
| 8,585,572 B2 | 11/2013 | Mehmanesh |
| 8,591,393 B2 | 11/2013 | Walters et al. |
| 8,597,170 B2 | 12/2013 | Walters et al. |
| 8,608,635 B2 | 12/2013 | Yomtov et al. |
| 8,617,239 B2 | 12/2013 | Reitan |
| 8,684,904 B2 | 4/2014 | Campbell et al. |
| 8,690,749 B1 | 4/2014 | Nunez |
| 8,721,516 B2 | 5/2014 | Scheckel |
| 8,721,517 B2 | 5/2014 | Zeng et al. |
| 8,727,959 B2 | 5/2014 | Reitan et al. |
| 8,734,331 B2 | 5/2014 | Evans et al. |
| 8,784,441 B2 | 7/2014 | Rosenbluth et al. |
| 8,790,236 B2 | 7/2014 | Larose et al. |
| 8,795,576 B2 | 8/2014 | Tao et al. |
| 8,801,590 B2 | 8/2014 | Mohl |
| 8,814,776 B2 | 8/2014 | Hastie et al. |
| 8,814,933 B2 | 8/2014 | Siess |
| 8,849,398 B2 | 9/2014 | Evans |
| 8,944,748 B2 | 2/2015 | Liebing |
| 8,992,406 B2 | 3/2015 | Corbett |
| 8,998,792 B2 | 4/2015 | Scheckel |
| 9,028,216 B2 | 5/2015 | Schumacher et al. |
| 9,089,634 B2 | 7/2015 | Schumacher et al. |
| 9,089,670 B2 | 7/2015 | Scheckel |
| 9,162,017 B2 | 10/2015 | Evans et al. |
| 9,217,442 B2 | 12/2015 | Wiessler et al. |
| 9,308,302 B2 | 4/2016 | Zeng |
| 9,314,558 B2 | 4/2016 | Er |
| 9,327,067 B2 | 5/2016 | Zeng et al. |
| 9,328,741 B2 | 5/2016 | Liebing |
| 9,358,330 B2 | 6/2016 | Schumacher |
| 9,381,288 B2 | 7/2016 | Schenck et al. |
| 9,421,311 B2 | 8/2016 | Tanner et al. |
| 9,446,179 B2 | 9/2016 | Keenan et al. |
| 2002/0010487 A1 | 1/2002 | Evans et al. |
| 2002/0047435 A1 | 4/2002 | Takahashi et al. |
| 2002/0094287 A1 | 7/2002 | Davis |
| 2002/0107506 A1 | 8/2002 | McGuckin et al. |
| 2002/0111663 A1 | 8/2002 | Dahl et al. |
| 2002/0151761 A1 | 10/2002 | Viole et al. |
| 2003/0018380 A1 | 1/2003 | Craig et al. |
| 2003/0023201 A1 | 1/2003 | Aboul-Hosn et al. |
| 2003/0100816 A1 | 5/2003 | Siess |
| 2003/0135086 A1 | 7/2003 | Khaw et al. |
| 2003/0187322 A1 | 10/2003 | Siess |
| 2003/0205233 A1 | 11/2003 | Aboul-Hosn et al. |
| 2003/0208097 A1 | 11/2003 | Aboul-Hosn et al. |
| 2003/0231959 A1 | 12/2003 | Snider |
| 2004/0010229 A1 | 1/2004 | Houde et al. |
| 2004/0044266 A1 | 3/2004 | Siess et al. |
| 2004/0101406 A1 | 5/2004 | Hoover |
| 2004/0113502 A1 | 6/2004 | Li et al. |
| 2004/0116862 A1 | 6/2004 | Ray |
| 2004/0152944 A1 | 8/2004 | Medvedev et al. |
| 2004/0253129 A1 | 12/2004 | Sorensen et al. |
| 2005/0049696 A1 | 3/2005 | Siess et al. |
| 2005/0085683 A1 | 4/2005 | Bolling et al. |
| 2005/0090883 A1 | 4/2005 | Westlund et al. |
| 2005/0095124 A1 | 5/2005 | Arnold et al. |

(56) References Cited

U.S. PATENT DOCUMENTS

| | | |
|---|---|---|
| 2005/0113631 A1 | 5/2005 | Bolling et al. |
| 2005/0135942 A1 | 6/2005 | Wood et al. |
| 2005/0137680 A1 | 6/2005 | Ortiz et al. |
| 2005/0165269 A9 | 7/2005 | Aboul Hosn et al. |
| 2005/0165466 A1 | 7/2005 | Morris et al. |
| 2005/0250975 A1 | 11/2005 | Carrier et al. |
| 2005/0277912 A1 | 12/2005 | John |
| 2006/0005886 A1 | 1/2006 | Parrino et al. |
| 2006/0008349 A1 | 1/2006 | Khaw |
| 2006/0018943 A1 | 1/2006 | Bechert et al. |
| 2006/0036127 A1 | 2/2006 | Delgado, III et al. |
| 2006/0058869 A1 | 3/2006 | Olson et al. |
| 2006/0062672 A1* | 3/2006 | McBride ............... F04D 29/026 416/142 |
| 2006/0063965 A1 | 3/2006 | Aboul-Hosn et al. |
| 2006/0089521 A1 | 4/2006 | Chang |
| 2006/0155158 A1 | 7/2006 | Aboul-Hosn |
| 2006/0167404 A1 | 7/2006 | Pirovano et al. |
| 2006/0264695 A1 | 11/2006 | Viole et al. |
| 2006/0270894 A1 | 11/2006 | Viole et al. |
| 2007/0100314 A1 | 5/2007 | Keren et al. |
| 2007/0142785 A1 | 6/2007 | Lundgaard et al. |
| 2007/0156006 A1 | 7/2007 | Smith et al. |
| 2007/0203442 A1 | 8/2007 | Bechert et al. |
| 2007/0212240 A1 | 9/2007 | Voyeux et al. |
| 2007/0217932 A1 | 9/2007 | Voyeux et al. |
| 2007/0217933 A1 | 9/2007 | Haser et al. |
| 2007/0233270 A1 | 10/2007 | Weber et al. |
| 2007/0237739 A1 | 10/2007 | Doty |
| 2007/0248477 A1 | 10/2007 | Nazarifar et al. |
| 2008/0004645 A1 | 1/2008 | To et al. |
| 2008/0004690 A1 | 1/2008 | Robaina |
| 2008/0031953 A1 | 2/2008 | Takakusagi et al. |
| 2008/0103442 A1 | 5/2008 | Kesten et al. |
| 2008/0103516 A1 | 5/2008 | Wulfman et al. |
| 2008/0103591 A1 | 5/2008 | Siess |
| 2008/0114339 A1 | 5/2008 | McBride et al. |
| 2008/0119943 A1 | 5/2008 | Armstrong et al. |
| 2008/0132748 A1 | 6/2008 | Shifflette |
| 2008/0167679 A1 | 7/2008 | Papp |
| 2008/0275290 A1 | 11/2008 | Viole et al. |
| 2008/0306327 A1 | 12/2008 | Shifflette |
| 2009/0018567 A1 | 1/2009 | Escudero et al. |
| 2009/0023975 A1 | 1/2009 | Marseille et al. |
| 2009/0024085 A1 | 1/2009 | To et al. |
| 2009/0053085 A1 | 2/2009 | Thompson et al. |
| 2009/0062597 A1 | 3/2009 | Shifflette |
| 2009/0073037 A1 | 3/2009 | Penna et al. |
| 2009/0087325 A1 | 4/2009 | Voltenburg, Jr. et al. |
| 2009/0093764 A1 | 4/2009 | Pfeffer et al. |
| 2009/0093765 A1 | 4/2009 | Glenn |
| 2009/0093796 A1 | 4/2009 | Pfeffer et al. |
| 2009/0099638 A1 | 4/2009 | Grewe |
| 2009/0112312 A1 | 4/2009 | Larose et al. |
| 2009/0118567 A1 | 5/2009 | Siess |
| 2009/0163864 A1 | 6/2009 | Breznock et al. |
| 2009/0171137 A1 | 7/2009 | Farnan et al. |
| 2009/0182188 A1 | 7/2009 | Marseille et al. |
| 2009/0234378 A1 | 9/2009 | Escudero et al. |
| 2010/0030161 A1 | 2/2010 | Duffy |
| 2010/0030186 A1 | 2/2010 | Stivland |
| 2010/0041939 A1 | 2/2010 | Siess |
| 2010/0047099 A1 | 2/2010 | Miyazaki et al. |
| 2010/0087773 A1 | 4/2010 | Ferrari |
| 2010/0094089 A1 | 4/2010 | Litscher et al. |
| 2010/0127871 A1 | 5/2010 | Pontin |
| 2010/0137802 A1 | 6/2010 | Yodfat et al. |
| 2010/0174239 A1 | 7/2010 | Yodfat et al. |
| 2010/0191035 A1 | 7/2010 | Kang et al. |
| 2010/0197994 A1 | 8/2010 | Mehmanesh |
| 2010/0210895 A1 | 8/2010 | Aboul-Hosn et al. |
| 2010/0268017 A1 | 10/2010 | Siess et al. |
| 2010/0274330 A1 | 10/2010 | Burwell et al. |
| 2010/0286210 A1 | 11/2010 | Murata et al. |
| 2010/0286791 A1 | 11/2010 | Goldsmith |
| 2011/0004046 A1 | 1/2011 | Campbell et al. |
| 2011/0004291 A1 | 1/2011 | Davis et al. |
| 2011/0009687 A1 | 1/2011 | Mohl |
| 2011/0015610 A1 | 1/2011 | Plahey et al. |
| 2011/0034874 A1 | 2/2011 | Reitan et al. |
| 2011/0071338 A1 | 3/2011 | McBride et al. |
| 2011/0076439 A1 | 3/2011 | Zeilon |
| 2011/0098805 A1 | 4/2011 | Dwork et al. |
| 2011/0106004 A1 | 5/2011 | Eubanks et al. |
| 2011/0152831 A1 | 6/2011 | Rotem et al. |
| 2011/0152906 A1 | 6/2011 | Escudero et al. |
| 2011/0152907 A1 | 6/2011 | Escudero et al. |
| 2011/0218516 A1 | 9/2011 | Grigorov |
| 2011/0237863 A1 | 9/2011 | Ricci et al. |
| 2011/0257462 A1 | 10/2011 | Rodefeld et al. |
| 2011/0270182 A1 | 11/2011 | Breznock et al. |
| 2011/0275884 A1 | 11/2011 | Scheckel |
| 2011/0300010 A1 | 12/2011 | Jarnagin et al. |
| 2012/0004495 A1 | 1/2012 | Bolling et al. |
| 2012/0029265 A1 | 2/2012 | LaRose et al. |
| 2012/0059213 A1 | 3/2012 | Spence et al. |
| 2012/0059460 A1 | 3/2012 | Reitan |
| 2012/0083740 A1 | 4/2012 | Chebator et al. |
| 2012/0142994 A1 | 6/2012 | Toellner |
| 2012/0172654 A1 | 7/2012 | Bates |
| 2012/0172655 A1 | 7/2012 | Campbell et al. |
| 2012/0172656 A1 | 7/2012 | Walters et al. |
| 2012/0178985 A1 | 7/2012 | Walters et al. |
| 2012/0178986 A1 | 7/2012 | Campbell et al. |
| 2012/0184803 A1 | 7/2012 | Simon et al. |
| 2012/0203056 A1 | 8/2012 | Corbett |
| 2012/0220854 A1 | 8/2012 | Messerly et al. |
| 2012/0224970 A1 | 9/2012 | Schumacher et al. |
| 2012/0226097 A1 | 9/2012 | Smith et al. |
| 2012/0234411 A1 | 9/2012 | Scheckel et al. |
| 2012/0237357 A1 | 9/2012 | Schumacher et al. |
| 2012/0245404 A1 | 9/2012 | Smith et al. |
| 2012/0265002 A1 | 10/2012 | Roehn et al. |
| 2013/0041202 A1 | 2/2013 | Toellner et al. |
| 2013/0053622 A1 | 2/2013 | Corbett |
| 2013/0053623 A1 | 2/2013 | Evans et al. |
| 2013/0066140 A1 | 3/2013 | McBride et al. |
| 2013/0085318 A1 | 4/2013 | Toellner et al. |
| 2013/0085319 A1 | 4/2013 | Evans et al. |
| 2013/0096364 A1 | 4/2013 | Reichenbach et al. |
| 2013/0103063 A1 | 4/2013 | Escudero et al. |
| 2013/0106212 A1 | 5/2013 | Nakazumi et al. |
| 2013/0129503 A1 | 5/2013 | McBride et al. |
| 2013/0138205 A1 | 5/2013 | Kushwaha et al. |
| 2013/0204362 A1 | 8/2013 | Toellner et al. |
| 2013/0209292 A1 | 8/2013 | Baykut et al. |
| 2013/0237744 A1 | 9/2013 | Pfeffer et al. |
| 2013/0245360 A1 | 9/2013 | Schumacher et al. |
| 2013/0303831 A1 | 11/2013 | Evans et al. |
| 2013/0303969 A1 | 11/2013 | Keenan et al. |
| 2013/0303970 A1 | 11/2013 | Keenan et al. |
| 2013/0331639 A1 | 12/2013 | Campbell et al. |
| 2013/0345492 A1 | 12/2013 | Pfeffer et al. |
| 2014/0005467 A1 | 1/2014 | Farnan et al. |
| 2014/0010686 A1 | 1/2014 | Tanner et al. |
| 2014/0012065 A1 | 1/2014 | Fitzgerald et al. |
| 2014/0039465 A1 | 2/2014 | Schulz et al. |
| 2014/0051908 A1 | 2/2014 | Khanal et al. |
| 2014/0067057 A1 | 3/2014 | Callaway et al. |
| 2014/0088455 A1 | 3/2014 | Christensen et al. |
| 2014/0148638 A1 | 5/2014 | LaRose et al. |
| 2014/0163664 A1 | 6/2014 | Goldsmith |
| 2014/0255176 A1 | 9/2014 | Bredenbreuker et al. |
| 2014/0275725 A1 | 9/2014 | Schenck et al. |
| 2014/0275726 A1 | 9/2014 | Zeng |
| 2014/0301822 A1 | 10/2014 | Scheckel |
| 2014/0303596 A1 | 10/2014 | Schumacher et al. |
| 2015/0025558 A1 | 1/2015 | Wulfman et al. |
| 2015/0031936 A1 | 1/2015 | Larose et al. |
| 2015/0051435 A1 | 2/2015 | Siess et al. |
| 2015/0051436 A1 | 2/2015 | Spanier et al. |
| 2015/0080743 A1 | 3/2015 | Siess et al. |
| 2015/0087890 A1 | 3/2015 | Spanier et al. |
| 2015/0141738 A1 | 5/2015 | Toellner et al. |

(56) References Cited

U.S. PATENT DOCUMENTS

| | | | |
|---|---|---|---|
| 2015/0141739 A1 | 5/2015 | Hsu et al. |
| 2015/0151032 A1 | 6/2015 | Voskoboynikov et al. |
| 2015/0209498 A1 | 7/2015 | Franano et al. |
| 2015/0250935 A1 | 9/2015 | Anderson et al. |
| 2015/0290372 A1 | 10/2015 | Muller et al. |
| 2015/0343179 A1 | 12/2015 | Schumacher et al. |
| 2016/0184500 A1 | 6/2016 | Zeng |
| 2016/0250399 A1 | 9/2016 | Tiller et al. |
| 2016/0250400 A1 | 9/2016 | Schumacher |
| 2016/0256620 A1 | 9/2016 | Schekel Mario et al. |

FOREIGN PATENT DOCUMENTS

| | | |
|---|---|---|
| EP | 0533432 A1 | 3/1993 |
| EP | 1207934 A2 | 5/2002 |
| EP | 1393762 A1 | 3/2004 |
| EP | 1591079 A1 | 11/2005 |
| EP | 2263732 A2 | 12/2010 |
| EP | 2298374 A1 | 3/2011 |
| FR | 2267800 A1 | 11/1975 |
| GB | 2239675 A | 7/1991 |
| JP | S48-23295 | 3/1973 |
| JP | S4823295 U | 3/1973 |
| JP | S58190448 A | 11/1983 |
| JP | H02211169 A | 8/1990 |
| JP | H06114101 A | 4/1994 |
| JP | H08196624 A | 8/1996 |
| JP | H1099447 A | 4/1998 |
| JP | H10099447 | 4/1998 |
| JP | 3208454 B2 | 9/2001 |
| TW | 500877 B2 | 9/2002 |
| WO | 8905164 A1 | 6/1989 |
| WO | 9526695 A2 | 10/1995 |
| WO | 9737697 A1 | 4/1996 |
| WO | 9715228 A1 | 5/1997 |
| WO | 12148 A2 | 3/2000 |
| WO | 0019097 A1 | 4/2000 |
| WO | 0043062 A1 | 7/2000 |
| WO | 61207 A1 | 10/2000 |
| WO | 0069489 A1 | 11/2000 |
| WO | 117581 A2 | 3/2001 |
| WO | 0124867 A1 | 4/2001 |
| WO | 02070039 A2 | 9/2002 |
| WO | 03103745 A2 | 12/2003 |
| WO | 2005089674 A1 | 9/2005 |
| WO | 2005123158 A1 | 12/2005 |
| WO | 2009073037 A1 | 6/2009 |
| WO | 2009076460 A2 | 6/2009 |
| WO | 2010127871 A1 | 11/2010 |
| WO | 2010133567 A1 | 11/2010 |
| WO | 2010149393 A1 | 12/2010 |
| WO | 2011035926 A1 | 3/2011 |
| WO | 2011035929 A2 | 3/2011 |
| WO | 2011039091 A1 | 4/2011 |
| WO | 2011076439 A1 | 6/2011 |
| WO | 2011089022 A1 | 7/2011 |
| WO | 2012007140 A1 | 1/2012 |
| WO | 2012007141 A1 | 1/2012 |
| WO | 2013148697 A1 | 10/2013 |
| WO | 2013160407 A1 | 10/2013 |
| WO | 2014019274 A1 | 2/2014 |
| WO | 2015063277 A2 | 5/2015 |

OTHER PUBLICATIONS

International Search Report and Written Opinion received in International Patent Application No. PCT/US2015/026025, dated Oct. 22, 2015, in 12 pages.
International Search Report and Written Opinion received in International Patent Application No. PCT/US2015/045370, dated Feb. 25, 2016, in 10 pages.
International Search Report and Written Opinion received in International Patent Application No. PCT/US2016/014371, dated Jul. 28, 2016, in 16 pages.
International Search Report and Written Opinion received in International Patent Application No. PCT/US2016/014379, dated Jul. 29, 2016, in 17 pages.
International Search Report and Written Opinion received in International Patent Application No. PCT/US2016/014391, dated Jul. 28, 2016, in 15 pages.
International Search Report and Written Opinion received in International Patent Application No. PCT/US2016/051553, dated Mar. 23, 2017, in 11 pages.
International Search Report received in International Patent Application No. PCT/US2003/004401, dated Jan. 22, 2004, in 7 pages.
International Search Report received in International Patent Application No. PCT/US2003/004853, dated Nov. 10, 2003, in 5 pages.
JOMED Reitan Catheter Pump RCP, Feb. 18, 2003, in 4 pages.
JOMED Reitan Catheter Pump RCP, Percutaneous Circulatory Support, in 10 pages, believed to be published prior to Oct. 15, 2003.
Krishnamani et al., "Emerging Ventricular Assist Devices for Long-Term Cardiac Support," National Review, Cardiology, Feb. 2010, pp. 71-76, vol. 7.
Kunst et al., "Integrated unit for programmable control of the 21F Hemopump and registration of physiological signals," Medical & Biological Engineering & Computing, Nov. 1994, pp. 694-696.
Mihaylov et al., "Development of a New Introduction Technique for the Pulsatile Catheter Pump," Artificial Organs, 1997, pp. 425-427; vol. 21(5).
Mihaylov et al., "Evaluation of the Optimal Driving Mode During Left Ventricular Assist with Pulsatile Catheter Pump in Calves," Artificial Organs, 1999, pp. 1117-1122; vol. 23(12).
Minimally Invasive Cardiac Assist JOMED Catheter PumpTM, in 6 pages, believed to be published prior to Jun. 16, 1999.
Morgan, "Medical Shape Memory Alloy Applications—The Market and its Products," Materials Science and Engineering, 2004, pp. 16-23, vol. A 378.
Morsink et al., "Numerical Modelling of Blood Flow Behaviour in the Valved Catheter of the PUCA-Pump, a LVAD,"The International Journal of Artificial Organs, 1997, pp. 277-284; vol. 20(5).
Nishimura et al, "The Enabler Cannula Pump: A Novel Circulatory Support System," The International Journal of Artificial Organs, 1999, pp. 317-323; vol. 22(5).
Nullity Action against the owner of the German part DE 50 2007 005 015.6 of European patent EP 2 047 872 B1, dated Jul. 13, 2015, in 61 pages.
Petrini et al., "Biomedical Applications of Shape Memory Alloys," Journal of Metallurgy, 2011, pp. 1-15.
Raess et al., "Impella 2.5," J. Cardiovasc. Transl. Res., 2009, pp. 168-172, vol. 2(2).
Reitan et al., "Hemodynamic Effects of a New Percutaneous Circulatory Support Device in a Left Ventricular Failure Model," ASAIO Journal, 2003, pp. 731-736, vol. 49.
Reitan et al., "Hydrodynamic Properties of a New Percutaneous Intra-Aortic Axial Flow Pump," ASAIO Journal 2000, pp. 323-328.
Reitan, Evaluation of a New Percutaneous Cardiac Assist Device, Department of Cardiology, Faculty of Medicine, Lund University, Sweden, 2002, in 172 pages.
Rothman, "The Reitan Catheter Pump: A New Versatile Approach for Hemodynamic Support", London Chest Hospital Barts & The London NHS Trust, Oct. 22-27, 2006 (TCT 2006: Transcatheter Cardiovascular Therapeutics 18th Annual Scientific Symposium, Final Program), in 48 pages.
Schmitz-Rode et al., "An Expandable Percutaneous Catheter Pump for Left Ventricular Support," Journal of the American College of Cardiology, 2005, pp. 1856-1861, vol. 45(11).
Shabari et al., "Improved Hemodynamics with a Novel Miniaturized Intra-Aortic Axial Flow Pump in a Porcine Model of Acute Left Ventricular Dysfunction," ASAIO Journal, 2013, pp. 240-245; vol. 59.
Sharony et al, "Cardiopulmonary Support and Physiology—The Intra-Aortic Cannula Pump: A Novel Assist Device for the Acutely Failing Heart," The Journal of Thoracic and Cardiovascular Surgery, Nov. 1992, pp. 924-929, vol. 118(5).

(56) References Cited

OTHER PUBLICATIONS

Sharony et al., "Right Heart Support During Off-Pump Coronary Artery Surgery—A Multi-Center Study," The Heart Surgery Forum, 2002, pp. 13-16, vol. 5(1).
Siess et al., "Basic design criteria for rotary blood pumps," H. Masuda, Rotary Blood Pumps, Springer, Japan, 2000, pp. 69-83.
Siess et al., "Concept, realization, and first in vitro testing of an intraarterial microaxial blood pump," Artificial Organs, 1995, pp. 644-652, vol. 19, No. 7, Blackwell Science, Inc., Boston, International Society for Artificial Organs.
Siess et al., "From a lab type to a product: A retrospective view on Impella's assist technology," Artificial Organs, 2001, pp. 414-421, vol. 25, No. 5, Blackwell Science, Inc., International Society for Artificial Organs.
Siess et al., "System analysis and development of intravascular rotation pumps for cardiac assist," Dissertation, Shaker Verlag, Aachen, 1999, 39 pages.
Sieß et al., "Hydraulic refinement of an intraarterial microaxial blood pump", The International Journal of Artificial Organs, 1995, vol. 18, No. 5, pp. 273-285.
Sieß , "Systemanalyse und Entwicklung intravasaler Rotationspumpen zur Herzunterstützung", Helmholtz-Institut fur Blomedixinische Technik an der RWTH Aachen, Jun. 24, 1998, in 105 pages.
Smith et al., "First-In-Man Study of the Reitan Catheter Pump for Circulatory Support in Patients Undergoing High-Risk Percutaneous Coronary Intervention," Catheterization and Cardiovascular Interventions, 2009, pp. 859-865, vol. 73(7).
Sokolowski et al., "Medical Applications of Shape Memory Polymers," Biomed. Mater. 2007, pp. S23-S27, vol. 2.
Stoeckel et al., "Self-Expanding Nitinol Stents—Material and Design Considerations," European Radiology, 2003, in 13 sheets.
Stolinski et al., "The heart-pump interaction: effects of a microaxial blood pump," International Journal of Artificial Organs, 2002, pp. 1082-1088, vol. 25, Issue 11.
Supplemental European Search Report received from the European Patent Office in EP Application No. EP 05799883 dated Mar. 19, 2010, 3 pages.
Takagaki et al., "A Novel Miniature Ventricular Assist Device for Hemodynamic Support," ASAIO Journal, 2001, pp. 412-416; vol. 47.
Throckmorton et al., "Flexible Impeller Blades in an Axial Flow Pump for Intravascular Cavopulmonary Assistance of the Fontan Physiology," Cardiovascular Engineering and Technology, Dec. 2010, pp. 244-255, vol. 1(4).
Throckmorton et al., "Uniquely shaped cardiovascular stents enhance the pressure generation of intravascular blood pumps," The Journal of Thoracic and Cardiovascular Surgery, Sep. 2012, pp. 704-709, vol. 133, No. 3.
Verkerke et al., "Numerical Simulation of the PUCA Pump, A Left Ventricular Assist Device," Abstracts of the XIXth ESAO Congress, The International Journal of Artificial Organs, 1992, p. 543, vol. 15(9).
Verkerke et al., "Numerical Simulation of the Pulsating Catheter Pump: A Left Ventricular Assist Device," Artificial Organs, 1999, pp. 924-931, vol. 23(10).
Verkerke et al., "The PUCA Pump: A Left Ventricular Assist Device," Artificial Organs, 1993, pp. 365-368, vol. 17(5).
Wampler et al., "The Sternotomy Hemopump, A Second Generation Intraarterial Ventricular Assist Device," ASAIO Journal, 1993, pp. M218-M223, vol. 39.
Weber et al., "Principles of Impella Cardiac Support," Supplemental to Cardiac Interventions Today, Aug./Sep. 2009.
Written Opinion received in International Patent Application No. PCT/US2003/04853, dated Feb. 25, 2004, 5 pages.
"Statistical Analysis and Clinical Experience with the Recover® Pump Systems", Impella CardioSystems GmbH, Sep. 2005, 2 sheets.
ABIOMED—Recovering Hearts. Saving Lives., Impella 2.5 System, Instructions for Use, Jul. 2007, in 86 sheets.

ABIOMED, "Impella 5.0 with the Impella Console, Circulatory Support System, Instructions for Use & Clinical Reference Manual," Jun. 2010, in 122 pages.
Aboul-Hosn et al., "The Hemopump: Clinical Results and Future Applications", Assisted Circulation 4, 1995, in 14 pages.
Barras et al., "Nitinol—Its Use in Vascular Surgery and Other Applications," Eur. J. Vasc. Endovasc. Surg., 2000, pp. 564-569; vol. 19.
Biscarini et al., "Enhanced Nitinol Properties for Biomedical Applications," Recent Patents on Biomedical Engineering, 2008, pp. 180-196, vol. 1(3).
Cardiovascular Diseases (CVDs) Fact Sheet No. 317; World Health Organization [Online], Sep. 2011. http://www.who.int/mediacentre/factsheets/fs317/en/index.html, accessed on Aug. 29, 2012.
Compendium of Technical and Scientific Information for the HEMOPUMP Temporary Cardiac Assist System, Johnson & Johnson Interventional Systems, 1988, in 15 pages.
Dekker et al., "Efficacy of a New Intraaortic Propeller Pump vs the Intraaortic Balloon Pump*, An Animal Study", Chest, Jun. 2003, vol. 123, No. 6, pp. 2089-2095.
Duerig et al., "An Overview of Nitinol Medical Applications," Materials Science Engineering, 1999, pp. 149-160; vol. A273.
European Search Report received in European Patent Application No. 05799883.3, dated May 10, 2011, in 4 pages.
Extended EP Search Report, dated Mar. 15, 2018, for related EP patent application No. EP 15833166.0, in 7 pages.
Extended European Search Report received in European Patent Application No. 07753903.9, dated Oct. 8, 2012, in 7 pages.
Extended European Search Report received in European Patent Application No. 13790890.1, dated Jan. 7, 2016, in 6 pages.
Extended European Search Report received in European Patent Application No. 13791118.6, dated Jan. 7, 2016, in 6 pages.
Extended European Search Report received in European Patent Application No. 13813687.4, dated Feb. 24, 2016, in 6 pages.
Extended European Search Report received in European Patent Application No. 13813867.2, dated Feb. 26, 2016, in 7 pages.
Extended European Search Report received in European Patent Application No. 14764392.8, dated Oct. 27, 2016, in 7 pages.
Extended European Search Report received in European Patent Application No. 14779928.2, dated Oct. 7, 2016, in 7 pages.
Federal and Drug Administration 510(k) Summary for Predicate Device IMPELLA 2.5 (K112892), prepared Sep. 5, 2012.
Grech, "Percutaneous Coronary Intervention. I: History and Development," BMJ., May 17, 2003, pp. 1080-1082, vol. 326.
Hsu et al., "Review of Recent Patents on Foldable Ventricular Assist Devices," Recent Patents on Biomedical Engineering, 2012, pp. 208-222, vol. 5.
Ide et al., "Evaluation of the Pulsatility of a New Pulsatile Left Ventricular Assist Device—the Integrated Cardioassist Catheter-in Dogs," J. of Thorac and Cardiovasc Sur, Feb. 1994, pp. 569-0575, vol. 107(2).
Ide et al., "Hemodynamic Evaluation of a New Left Ventricular Assist Device: An Integrated Cardioassist Catheter as a Pulsatile Left Ventricle-Femoral Artery Bypass," Blackwell Scientific Publications, Inc., 1992, pp. 286-290, vol. 16(3).
Impella CP®—Instructions for Use & Clinical Reference Manual (United States only), Abiomed, Inc., Jul. 2014, 148 pages, www.abiomed.com.
Impella LD® with the Impella® Controller—Circulatory Support System—Instructions for Use & Clinical Reference Manual (United States only), Abiomed, Inc., Sep. 2010, 132 pages, www.abiomed.com.
International Preliminary Examination Report received in International Patent Application No. PCT/US2003/04401, dated May 18, 2004, in 4 pages.
International Preliminary Examination Report received in International Patent Application No. PCT/US2003/04853, dated Jul. 26, 2004, in 5 pages.
International Preliminary Report on Patentability and Written Opinion of the International Searching Authority received in International Patent Application No. PCT/US2005/033416, dated Mar. 20, 2007, in 7 pages.

(56) References Cited

OTHER PUBLICATIONS

International Preliminary Report on Patentability and Written Opinion of the International Searching Authority received in International Patent Application No. PCT/US2007/007313, dated Sep. 23, 2008, in 6 pages.
International Preliminary Report on Patentability and Written Opinion received in International Patent Application No. PCT/US2014/020878, dated Sep. 15, 2015, in 8 pages.
International Search Report and Written Opinion received in International Patent Application No. PCT/US2005/033416, dated Dec. 11, 2006, in 8 pages.
International Search Report and Written Opinion received in International Patent Application No. PCT/US2007/007313, dated Mar. 4, 2008, in 6 pages.
International Search Report and Written Opinion received in International Patent Application No. PCT/US2010/040847, dated Jan. 6, 2011, in 15 pages.
International Search Report and Written Opinion received in International Patent Application No. PCT/US2012/020369, dated Jul. 30, 2012, in 10 pages.
International Search Report and Written Opinion received in International Patent Application No. PCT/US2012/020382, dated Jul. 31, 2012, in 11 pages.
International Search Report and Written Opinion received in International Patent Application No. PCT/US2012/020383, dated Aug. 17, 2012; in 9 pages.
International Search Report and Written Opinion received in International Patent Application No. PCT/US2012/020553, dated Aug. 17, 2012, in 8 pages.
International Search Report and Written Opinion received in International Patent Application No. PCT/US2013/040798, dated Aug. 21, 2013, in 16 pages.
International Search Report and Written Opinion received in International Patent Application No. PCT/US2013/040799, dated Aug. 21, 2013, in 19 pages.
International Search Report and Written Opinion received in International Patent Application No. PCT/US2013/040809, dated Sep. 2, 2013, in 25 pages.
International Search Report and Written Opinion received in International Patent Application No. PCT/US2013/048332, dated Oct. 16, 2013, in 14 pages.
International Search Report and Written Opinion received in International Patent Application No. PCT/US2013/048343, dated Oct. 11, 2013, in 15 pages.
International Search Report and Written Opinion received in International Patent Application No. PCT/US2014/020790, dated Oct. 9, 2014, in 9 pages.
International Search Report and Written Opinion received in International Patent Application No. PCT/US2014/020878, dated May 7, 2014, in 11 pages.
International Search Report and Written Opinion received in International Patent Application No. PCT/US2015/025959, dated Oct. 22, 2015, in 9 pages.
International Search Report and Written Opinion received in International Patent Application No. PCT/US2015/025960, dated Oct. 22, 2015, in 11 pages.
International Search Report and Written Opinion received in International Patent Application No. PCT/US2015/026013, dated Oct. 22, 2015, in 8 pages.
International Search Report and Written Opinion received in International Patent Application No. PCT/US2015/026014, dated Oct. 22, 2015, in 8 pages.

* cited by examiner

IMPELLER FOR CATHETER PUMP

INCORPORATION BY REFERENCE TO ANY PRIORITY APPLICATIONS

The present application is a Continuation of U.S. patent application Ser. No. 15/589,366, filed on May 8, 2017, and issued as U.S. patent Ser. No. 10,039,872, which is a Continuation of U.S. patent application Ser. No. 15/142,522, filed on Apr. 29, 2016, and issued as U.S. Pat. No. 9,675,740, which is a Continuation of U.S. patent application Ser. No. 14/401,096, filed on Nov. 13, 2014 and issued as U.S. Pat. No. 9,327,067, which claims the benefit of priority to P.C.T. Application No. PCT/US2013/040809, filed on May 13, 2013, which claims the benefit of priority to U.S. patent application Ser. No. 13/802,570, filed on Mar. 13, 2013 and issued as U.S. Pat. No. 8,721,517, which claims the benefit of priority to U.S. Provisional Patent Application No. 61/667,875, filed on Jul. 3, 2012, and U.S. Provisional Patent Application No. 61/646,827, filed on May 14, 2012, all of which are hereby incorporated by reference herein. Any and all applications not listed above for which a foreign or domestic priority claim is identified in the Application Data Sheet as filed with the present application are hereby incorporated by reference under 37 CFR 1.57.

BACKGROUND OF THE INVENTION

Field of the Invention

This application is directed to pumps for mechanical circulatory support of a heart. In particular, this application is directed to various implementations of an impeller that can be used in a catheter pump.

Description of the Related Art

Heart disease is a major health problem that has high mortality rate. Physicians increasingly use mechanical circulatory support systems for treating heart failure. The treatment of acute heart failure requires a device that can provide support to the patient quickly. Physicians desire treatment options that can be deployed quickly and minimally-invasively.

Intra-aortic balloon pumps (IABP) are currently the most common type of circulatory support devices for treating acute heart failure. IABPs are commonly used to treat heart failure, such as to stabilize a patient after cardiogenic shock, during treatment of acute myocardial infarction (MI) or decompensated heart failure, or to support a patient during high risk percutaneous coronary intervention (PCI). Circulatory support systems may be used alone or with pharmacological treatment.

In a conventional approach, an IABP is positioned in the aorta and actuated in a counterpulsation fashion to provide partial support to the circulatory system. More recently minimally-invasive rotary blood pump have been developed in an attempt to increase the level of potential support (i.e. higher flow). A rotary blood pump is typically inserted into the body and connected to the cardiovascular system, for example, to the left ventricle and the ascending aorta to assist the pumping function of the heart. Other known applications pumping venous blood from the right ventricle to the pulmonary artery for support of the right side of the heart. An aim of acute circulatory support devices is to reduce the load on the heart muscle for a period of time, to stabilize the patient prior to heart transplant or for continuing support.

There is a need for improved mechanical circulatory support devices for treating acute heart failure. Fixed cross-section ventricular assist devices designed to provide near full heart flow rate are either too large to be advanced percutaneously (e.g., through the femoral artery without a cutdown) or provide insufficient flow.

There is a need for a pump with improved performance and clinical outcomes. There is a need for a pump that can provide elevated flow rates with reduced risk of hemolysis and thrombosis. There is a need for a pump that can be inserted minimally-invasively and provide sufficient flow rates for various indications while reducing the risk of major adverse events. In one aspect, there is a need for a heart pump that can be placed minimally-invasively, for example, through a 15FR or 12FR incision. In one aspect, there is a need for a heart pump that can provide an average flow rate of 4 Lpm or more during operation, for example, at 62 mmHg of head pressure. While the flow rate of a rotary pump can be increased by rotating the impeller faster, higher rotational speeds are known to increase the risk of hemolysis, which can lead to adverse outcomes and in some cases death. Accordingly, in one aspect, there is a need for a pump that can provide sufficient flow at significantly reduced rotational speeds. These and other problems are overcome by the inventions described herein.

SUMMARY

There is an urgent need for a pumping device that can be inserted percutaneously and also provide full cardiac rate flows of the left, right, or both the left and right sides of the heart when called for.

In one embodiment, an impeller for a pump is disclosed. The impeller can comprise a hub having a proximal end portion and a distal end portion. A blade can be supported by the hub. The blade can have a fixed end coupled to the hub and a free end. Further, the impeller can have a stored configuration when the impeller is at rest, a deployed configuration when the impeller is at rest, and an operational configuration when the impeller rotates. The blade in the deployed and operational configurations can extend away from the hub. The blade in the stored configuration can be compressed against the hub. The blade can include a curved surface having a radius of curvature. The radius of curvature can be larger in the operational configuration than when the impeller is in the deployed configuration.

In another embodiment, a percutaneous heart pump is disclosed. The pump can comprise a catheter body and an impeller coupled to a distal end portion of the catheter body. The impeller can comprise a hub. A blade can be supported by the hub and can have a front end portion and a back end portion. The blade can include a ramped surface at the back end portion. A sheath can be disposed about the catheter body and can have a proximal end and a distal end. The distal end of the sheath can be configured to compress the blade from an expanded configuration to a stored configuration when the distal end of the sheath is urged against the ramped surface of the blade.

In yet another embodiment, a method for storing an impeller is disclosed. The method can comprise urging a sheath against a ramped surface of a back end of a blade of an impeller. The impeller can have one or more blades. Further, the impeller can have a stored configuration and a deployed configuration. Each blade in the stored configuration can be compressed against a hub of the impeller. Each blade in the deployed configuration can extend away from the hub. The method can further comprise collapsing the blade against the hub to urge the impeller into the stored configuration.

In another embodiment, a percutaneous heart pump system is disclosed. The system can comprise an impeller disposed at a distal portion of the system. The impeller can be sized and shaped to be inserted through a vascular system of a patient. The impeller can be configured to pump blood through at least a portion of the vascular system at a flow rate of at least about 3.5 liters per minute when the impeller is rotated at a speed less than about 21,000 revolutions per minute.

In another embodiment, a method of pumping blood through the vascular system of a patient is disclosed. The method can comprise inserting an impeller through a portion of the vascular system of the patient to a heart chamber. The method can further include rotating the impeller at a speed less than about 21,000 revolutions per minute to pump blood through at least a portion of the vascular system at a flow rate of at least about 3.5 liters per minute.

In yet another embodiment, an impeller configured for use in a catheter pump is disclosed. The impeller can comprise a hub having a distal portion, a proximal portion, and a diameter. The impeller can also include a blade having a fixed end at the hub and a free end. The blade can have a height defined by a maximum distance between the hub and the free end. A value relating to a ratio of the blade height to the hub diameter can be in a range of about 0.7 to about 1.45.

In another embodiment, a percutaneous heart pump system is disclosed. The system can comprise an impeller disposed at a distal portion of the system, the impeller sized and shaped to be inserted into a vascular system of a patient through a percutaneous access site having a size less than about 21 FR. The impeller can be configured to pump blood in the vascular system at a flow rate of at least about 3.5 liters per minute.

In another embodiment, a percutaneous heart pump system is disclosed. The system can include an impeller comprising one or more blades in a single row. The impeller can be disposed at a distal portion of the system. The impeller can be sized and shaped to be inserted through a vascular system of a patient. The impeller can be configured to pump blood through at least a portion of the vascular system at a flow rate of at least about 2.0 liters per minute when the impeller is rotated at a speed less than about 21,000 revolutions per minute.

BRIEF DESCRIPTION OF THE DRAWINGS

A more complete appreciation of the subject matter of this application and the various advantages thereof can be realized by reference to the following detailed description, in which reference is made to the accompanying drawings in which.

Figure 1:
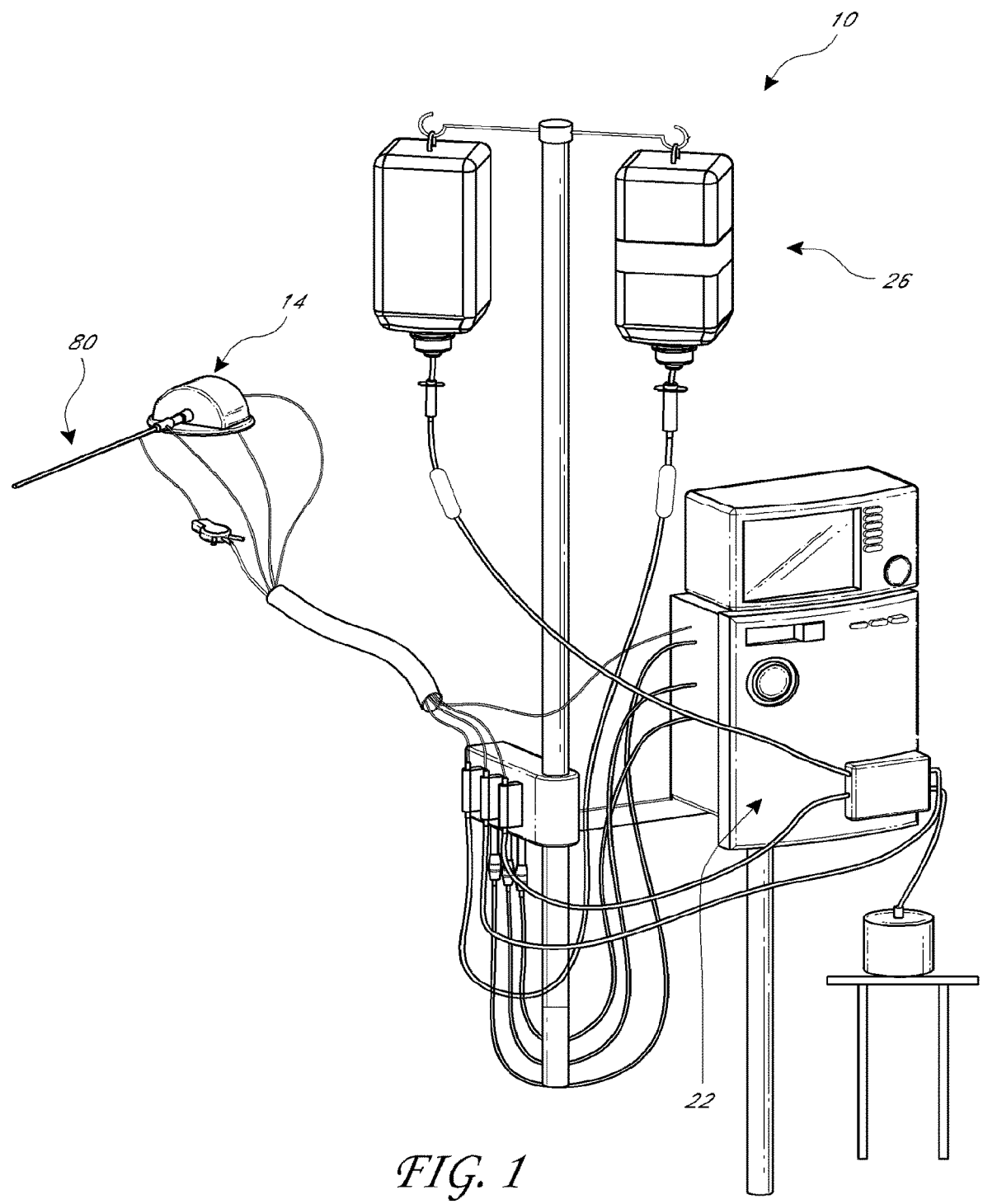
FIG. 1 illustrates one embodiment of a catheter pump configured for percutaneous application and operation.

More detailed descriptions of various embodiments of components for heart pumps useful to treat patients experiencing cardiac stress, including acute heart failure, are set forth below.

DETAILED DESCRIPTION

This application is directed to apparatuses for inducing motion of a fluid relative to the apparatus. In particular, the disclosed embodiments generally relate to various configurations for an impeller disposed at a distal portion of a percutaneous catheter pump. For example, FIGS. 1-4 show aspects of an exemplary catheter pump 10 that can provide high performance flow rates. The exemplary pump 10 includes a motor driven by a controller 22. The controller 22 directs the operation of the motor 14 and an infusion system 26 that supplies a flow of infusant or infusate in the pump 10. A catheter system 80 that can be coupled with the motor 14 houses an impeller within a distal portion thereof. In various embodiments, the impeller is rotated remotely by the motor 14 when the pump 10 is operating. For example, the motor 14 can be disposed outside the patient. In some embodiments, the motor 14 is separate from the controller 22, e.g., to be placed closer to the patient. In other embodiments, the motor 14 is part of the controller 22. In still other embodiments, the motor is miniaturized to be insertable into the patient. Such embodiments allow the drive shaft to be much shorter, e.g., shorter than the distance from the aortic valve to the aortic arch (about 5 cm or less). Some examples of miniaturized motors catheter pumps and related components and methods are discussed in U.S. Pat. Nos. 5,964,694; 6,007,478; 6,178,922; and 6,176,848, all of which are hereby incorporated by reference herein in their entirety for all purposes.

Figure 4:
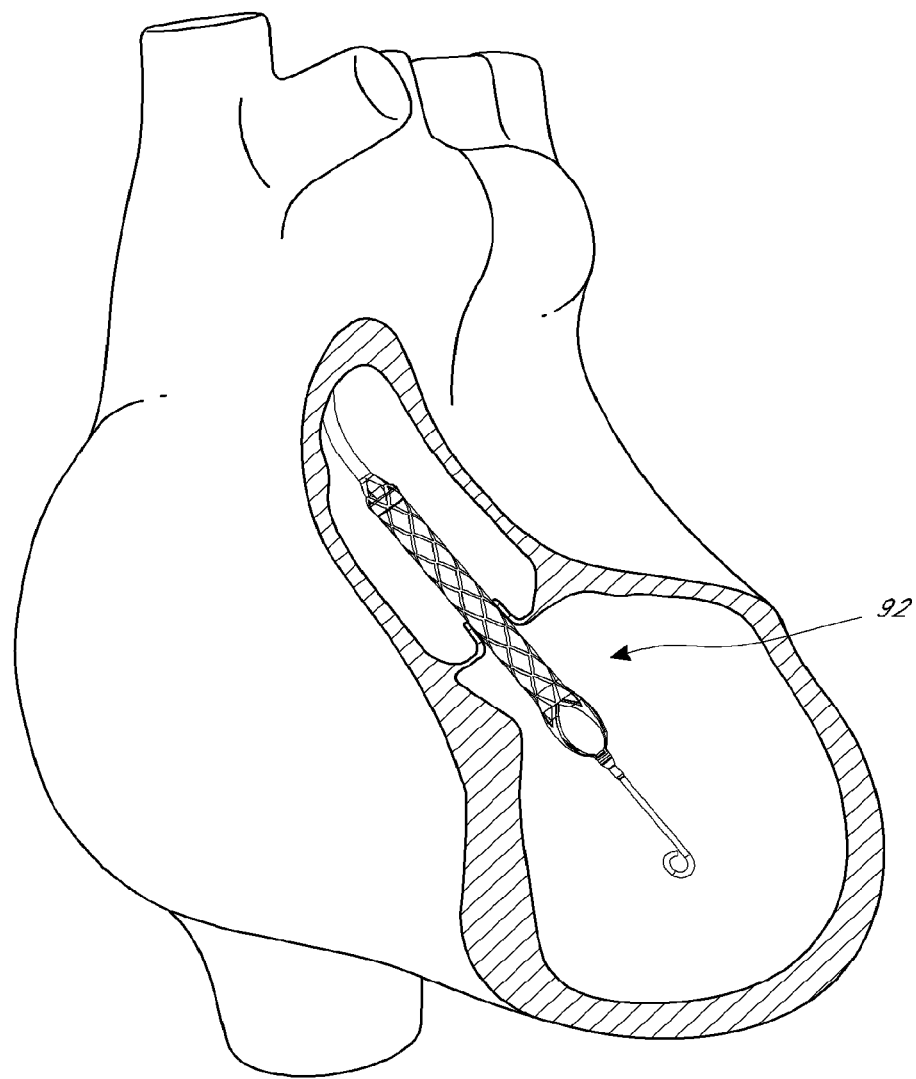
FIG. 4 shows the catheter assembly similar to that of FIG. 2 in position within the anatomy.

FIG. 4 illustrates one use of the exemplary catheter pump 10. A distal portion of the pump 10, which can include an impeller assembly 92, is placed in the left ventricle (LV) of the heart to pump blood from the LV into the aorta. The pump 10 can be used in this way to treat patients with a wide range of conditions, including cardiogenic shock, myocardial infarction, and other cardiac conditions, and also to support a patient during a procedure such as percutaneous coronary intervention. One convenient manner of placement of the distal portion of the pump 10 in the heart is by percutaneous access and delivery using the Seldinger technique or other methods familiar to cardiologists. These approaches enable the pump 10 to be used in emergency medicine, a catheter lab and in other non-surgical settings. Modifications can also enable the pump 10 to support the right side of the heart. Example modifications that could be used for right side support include providing delivery features and/or shaping a distal portion that is to be placed through at least one heart valve from the venous side, such as is discussed in U.S. Pat. Nos. 6,544,216; 7,070,555; and US 2012-0203056A1, all of which are hereby incorporated by reference herein in their entirety for all purposes.

Figure 2:
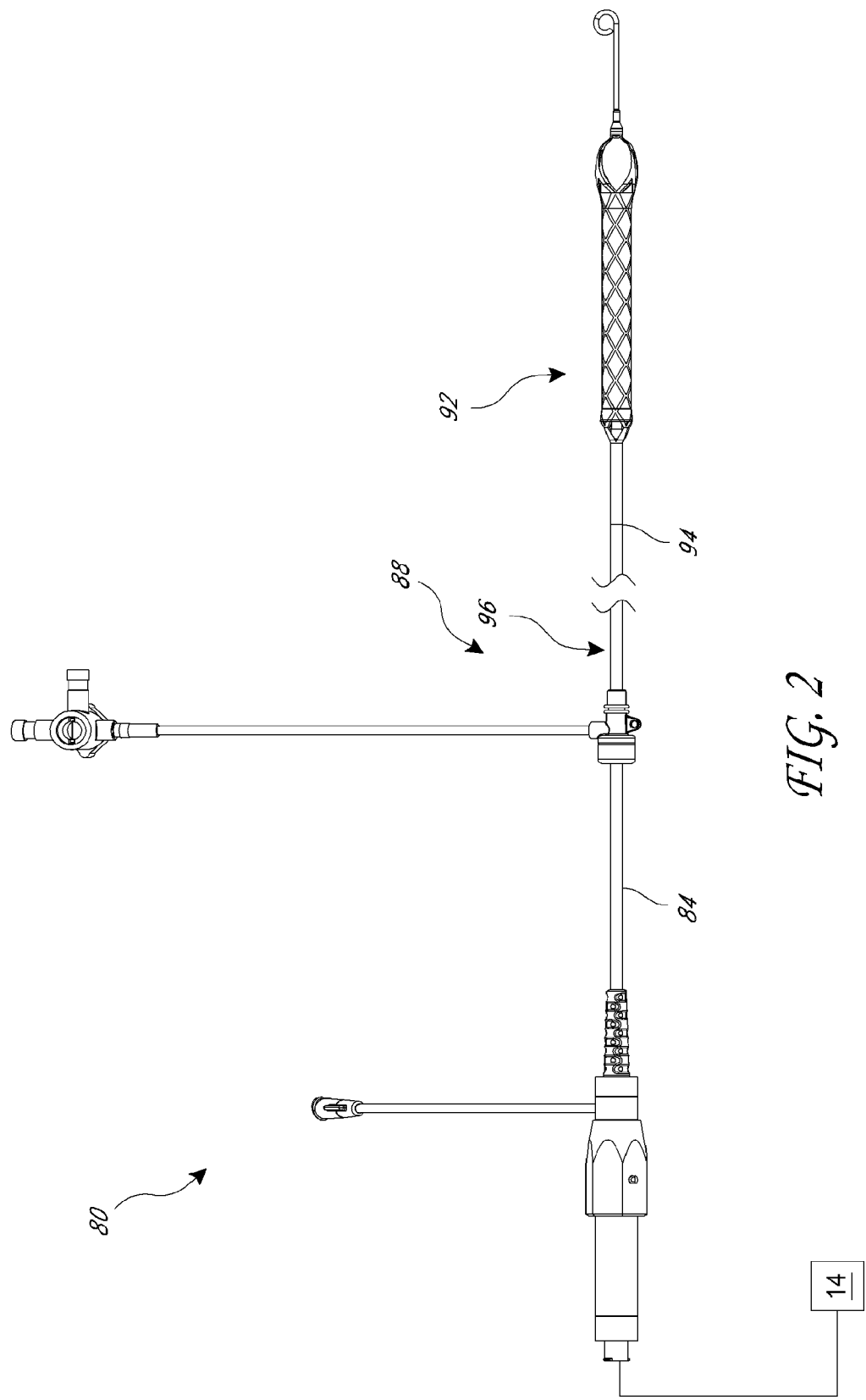
FIG. 2 is a plan view of one embodiment of a catheter adapted to be used with the catheter pump of FIG. 1.
Figure 3:
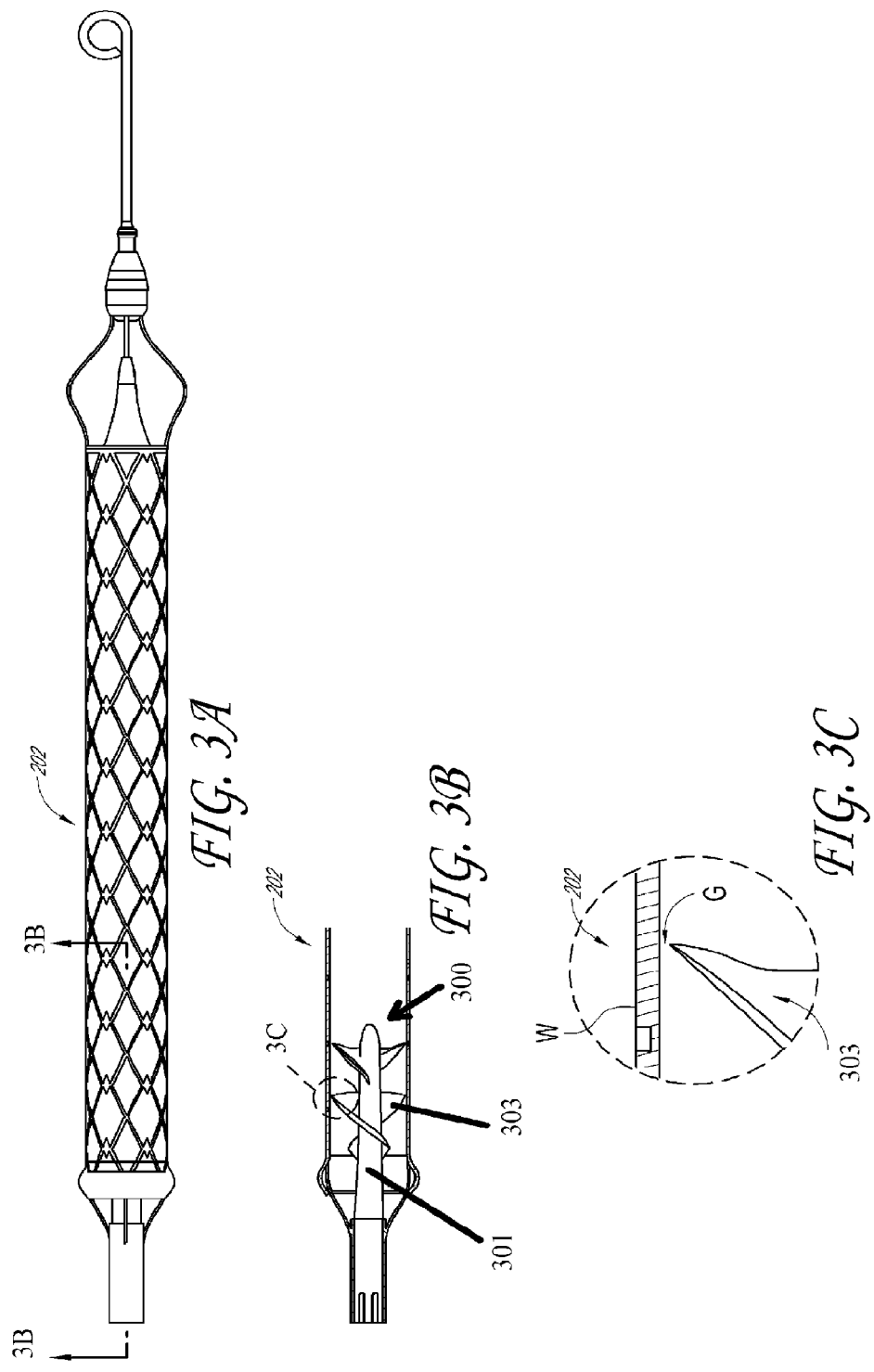
FIGS. 3A-3C illustrate the relative position of an impeller blade and an inner surface of an impeller housing in an undeflected configuration.

FIG. 2 shows features that facilitate small blood vessel percutaneous delivery and high performance, including up to and in some cases exceeding normal cardiac output in all phases of the cardiac cycle. In particular, the catheter system 80 includes a catheter body 84 and a sheath assembly 88. The impeller assembly 92 is coupled with the distal end of the catheter body 84. The exemplary impeller assembly 92 is expandable and collapsible. In the collapsed state, the distal end of the catheter system 80 can be advanced to the heart, for example, through an artery. In the expanded state, the impeller assembly 92 is able to pump blood at high flow rates. FIGS. 2-4 illustrate the expanded state. The collapsed state can be provided by advancing a distal end 94 of an elongate body 96 distally over the impeller assembly 92 to cause the impeller assembly 92 to collapse. This provides an outer profile throughout the catheter assembly 80 that is of small diameter, for example, to a catheter size of about 12.5 FR in various arrangements. Although various expandable impellers are disclosed herein (e.g., impellers having a stored configuration and a deployed configuration), it should be appreciated that the principles described below may also be applicable to impellers that may not be expandable or collapsible. For example, the impeller parameters described herein may also be applicable to fixed diameter impellers in some arrangements.

In some embodiments, the impeller assembly 92 includes a self-expanding material that facilitates expansion. The catheter body 84 on the other hand preferably is a polymeric body that has high flexibility. When the impeller assembly 92 is collapsed, as discussed above, high forces are applied to the impeller assembly 92. These forces are concentrated at a connection zone, where the impeller assembly 92 and the catheter body 84 are coupled together. These high forces, if not carefully managed can result in damage to the catheter assembly 80 and in some cases render the impeller within the impeller assembly 92 inoperable. Robust mechanical interface, are provided to assure high performance.

The mechanical components rotatably supporting the impeller within the impeller assembly 92 permit high rotational speeds while controlling heat and particle generation that can come with high speeds. The infusion system 26 delivers a cooling and lubricating solution to the distal portion of the catheter system 80 for these purposes. However, the space for delivery of this fluid is extremely limited. Some of the space is also used for return of the infusate. Providing secure connection and reliable routing of infusate into and out of the catheter assembly 80 is critical and challenging in view of the small profile of the catheter body 84.

When activated, the pump 10 can effectively increase the flow of blood out of the heart and through the patient's vascular system. In various embodiments disclosed herein, the pump 10 can be configured to produce a maximum flow rate (e.g. low mm Hg) of greater than 4 Lpm, greater than 4.5 Lpm, greater than 5 Lpm, greater than 5.5 Lpm, greater than 6 Lpm, greater than 6.5 Lpm, greater than 7 Lpm, greater than 7.5 Lpm, greater than 8 Lpm, greater than 9 Lpm, or greater than 10 Lpm. In various embodiments, the pump can be configured to produce an average flow rate at about 62 mmHg during operation of greater than 2 Lpm, greater than 2.5 Lpm, greater than 3 Lpm, greater than 3.5 Lpm, greater than 4 Lpm, greater than 4.5 Lpm, greater than 5 Lpm, greater than 5.5 Lpm, or greater than 6 Lpm. In various embodiments, the pump can be configured to produce an average flow rate of at least about 4.25 Lpm at 62 mmHg. In various embodiments, the pump can be configured to produce an average flow rate of at least about 4 Lpm at 62 mmHg. In various embodiments, the pump can be configured to produce an average flow rate of at least about 4.5 Lpm at 62 mmHg.

Various aspects of the pump and associated components are similar to those disclosed in U.S. Pat. Nos. 7,393,181, 8,376,707, 7,841,976, 7,022,100, and 7,998,054 and U.S. Pub. Nos. 2011/0004046, 2012/0178986, 2012/0172655, 2012/0178985, and 2012/0004495, the entire contents of which are incorporated herein for all purposes by reference. In addition, this application incorporates by reference in its entirety and for all purposes the subject matter disclosed in each of the following concurrently filed applications: U.S. patent application Ser. No. 13/802,556 entitled "DISTAL BEARING SUPPORT," filed on Mar. 13, 2013; U.S. Patent Application No. 61/780,656, entitled "FLUID HANDLING SYSTEM," filed on Mar. 13, 2013; U.S. patent application Ser. No. 13/801,833, entitled "SHEATH SYSTEM FOR CATHETER PUMP," filed on Mar. 13, 2013; U.S. patent application Ser. No. 13/801,833, entitled "CATHETER PUMP," filed on Mar. 13, 2013; and U.S. patent application Ser. No. 13/802,468, entitled "MOTOR ASSEMBLY FOR CATHETER PUMP," filed on Mar. 13, 2013.

Blade & Impeller Configurations

With reference to FIGS. 3A-3C, an operative device of the pump can include an impeller 300 having one or more blades 303. The one or more blades 303 can extend from an impeller hub 301. It can be desirable to increase the flow rate of the heart pump while ensuring that the impeller 300 can be effectively deployed within a subject. For example, an impeller can include one or more blades 303 that are configured to be inserted into a subject in a stored, or compressed, configuration. When the impeller 300 is positioned in the desired location, e.g., a chamber of a subject's heart as shown in FIG. 4, the blade(s) 303 of the impeller 300 can self-expand into a deployed or expanded configuration, in which the blade(s) 303 extends radially from a hub 301.

As shown in FIGS. 3A-3B, the impeller 300 can be positioned within a cannula or housing 202. A free end of the blades 303 can be separated from the wall W of the housing 202 by a tip gap G. The housing 202 can also have a stored, or compressed configuration, and a deployed or expanded configuration. The housing 202 and impeller 300 may deploy from the stored configurations from within a sheath or sleeve (not shown) into the expanded configuration. In such implementations, the sheath or sleeve can keep the blade(s) 303 and the housing 202 compressed until the blade(s) 303 and housing 202 are urged from within a storage cavity of the sheath or sleeve. Once the blade(s) 303 are released from the storage cavity of the sheath, the blade(s) 303 can self-expand to a deployed configuration using strain energy stored in the blades 303 due to deformation of the blade(s) 303 within the sheath or sleeve. The expandable housing 202 may also self-deploy using stored strain energy after being urged from the sheath.

In the stored configuration, the impeller 300 and housing 202 have a diameter that is preferably small enough to be inserted percutaneously into a patient's vascular system. Thus, it can be advantageous to fold the impeller 300 and housing 202 into a small enough stored configuration such that the housing 202 and impeller 300 can fit within the patient's veins or arteries. In some embodiments, therefore, the impeller 300 can have a diameter in the stored configuration corresponding to a catheter size between about 8 FR and about 21 FR. In one implementation, the impeller 300 can have a diameter in the stored state corresponding to a catheter size of about 9 FR. In other embodiments, the impeller 300 can have a diameter in the stored configuration between about 12 FR and about 21 FR. For example, in one embodiment, the impeller 300 can have a diameter in the stored configuration corresponding to a catheter size of about 12 FR or about 12.5 FR.

When the impeller 300 is positioned within a chamber of the heart, however, it can be advantageous to expand the impeller 300 to have a diameter as large as possible in the expanded or deployed configuration. In general, increased diameter of the impeller 300 can advantageously increase flow rate through the pump. In some implementations, the impeller 300 can have a diameter corresponding to a catheter size greater than about 12 FR in the deployed configuration. In other embodiments, the impeller 300 can have a diameter corresponding to a catheter size greater than about 21 FR in the deployed or expanded configuration.

In various embodiments, it can be important to increase the flow rate of the heart pump while ensuring that the operation of the pump does not harm the subject. For example, increased flow rate of the heart pump can advantageously yield better outcomes for a patient by improving the circulation of blood within the patient. Furthermore, the pump should avoid damaging the subject. For example, if the pump induces excessive shear stresses on the blood and fluid flowing through the pump (e.g., flowing through the cannula), then the impeller can cause damage to blood cells, e.g., hemolysis. If the impeller damages a large number of blood cells, then hemolysis can lead to negative outcomes for the subject, or even death. As will be explained below, various blade parameters can affect the pump's flow rate as well as conditions within the subject's body.

Overview of Various Embodiments

Various embodiments of an impeller for use in a heart pump are disclosed herein. In particular, FIGS. 5A-11 illustrate different configurations for an impeller 300-300J. Each of the disclosed impellers 300-300J can be defined by several different characteristics or parameters that can advantageously improve flow rate while achieving healthy outcomes in a patient. Further, various properties or characteristics of the disclosed impellers may assist in storing and/or deploying the impeller into and/or out from an outer sleeve. Each figure may only illustrate a few of the characteristics of the impeller for ease of illustration. However, it should be appreciated that each illustrated impeller may be associated with all of the characteristics or properties disclosed herein. For example, some figures may illustrate only a few angles or other geometric or structural properties of the impeller, but it should be appreciated that all the impellers disclosed herein may be associated with the disclosed characteristics or properties (see, e.g., the example values given in Tables 1 and 2).

In order to improve patient outcomes, it can be advantageous to provide a heart pump capable of pumping blood at high flow rates while minimizing damage to the blood or the patient's anatomy. For example, it can be desirable to increase flow rate while reducing the motor speed, as higher motor speeds are known to increase the hemolysis risk. Furthermore, for percutaneous insertion heart pump systems, it can be advantageous to make the diameter of the impeller and the cannula as small as possible for insertion into the patient's vasculature. Accordingly, the various impeller embodiments disclosed herein can provide high flow rate while maintaining a diameter small enough for insertion into the patient's vasculature and while reducing the risk that the patient's anatomy and blood are damaged during operation of the pump.

For some or all of the impellers 300-300J illustrated in FIGS. 5A-11, for example, the blades 303 may be formed to have a curved profile with a radius of curvature, R. The radius of curvature R may be sized such that, when the impeller is in the stored or compressed configuration, the blades 303 conform closely to the hub 301. Indeed, in various arrangements, the blades 303 in the stored configuration can have a radius $R_S$ sized such that the blades 303 lie against the hub 301 in a low profile so that the insertion diameter of the catheter pump is small enough to be safely inserted through the patient's vasculature. In some embodiments, the radius of curvature R and/or the height h of the blade 303 are selected such that neighboring blades in a particular blade row do not overlap when the impeller is in the stored configuration. By reducing or eliminating blade overlap in the stored configuration, the insertion diameter of the catheter pump can be reduced. In other arrangements, however, neighboring blades may overlap in the stored configuration.

Furthermore, when the impeller is urged out of an external sleeve, the impeller can self-expand into a deployed configuration, in which the impeller is deployed from the sleeve and expanded into a deployed diameter larger than a stored diameter. In various embodiments, the self-expansion of the impeller can be induced by strain energy stored in the blades 303, such as strain or potential energy stored near the root of the blades 303. When the sleeve is urged away from the impeller, the blades 303 can be free to expand into the deployed configuration. It should be appreciated that when the blades 303 are in the deployed configuration, the blade(s) 303 can be in a relaxed state, such that there are no or minimal external forces (such as torque- or flow-induced loads) and internal forces (such as strain energy stored in the blades) applied to the impeller or blades. A radius of curvature $R_D$ of the blades 303 in the deployed configuration may be selected to improve flow characteristics of the pump while reducing the risk of hemolysis or other damage to the patient. For example, in some embodiments, the impeller can be molded to form blades 303 having the desired deployed radius of curvature $R_D$, such that in a relaxed (e.g., deployed) state, the blades 303 have a radius of curvature $R_D$ that may be selected during manufacturing (e.g., molding). In some arrangements, the radius of curvature $R_D$ of the blades in the deployed configuration may be about the same as the radius of curvature $R_S$ of the blades in the stored configuration. In other arrangements, however, the radius of curvature of the blades 303 in the stored and deployed configurations may be different.

When the heart pump is activated to rotate the impeller, the impeller and blades 303 may be in an operational configuration. In the operational configuration, the impeller may rotate to drive blood through the housing 202. The rotation of the impeller and/or the flow of blood past the impeller can cause the blades 303 to deform such that an operational radius of curvature $R_o$ may be induced when the impeller is in the operational configuration. For example, when the impeller rotates, the blades 303 may slightly elongate such that the free ends of the blades 303 extend further radially from the hub 301 relative to when the blades 303 are in the deployed configuration. As the blades 303 deform radially outward in the operational configuration, the operational radius of curvature $R_o$ may therefore be larger than the deployed radius of curvature $R_D$. For example, in some embodiments, in the operational configuration, the blades 303 may substantially flatten such that there is little curvature of the blades during operation of the pump. Indeed, in the operational configuration, the blades 303 may extend to an operational height $h_o$ that is larger than the height h of the blades 303 when in the deployed configuration (see h as illustrated in the impellers 300-300J of FIG. 5A-11, which are in a deployed or relaxed configuration). In some embodiments, because the blades 303 may be manufactured to be relaxed when in the deployed configuration, the radius of curvature $R_D$ and the height h of the blades 303 in the deployed configuration can be selected such that, in the operational configuration, the blades 303 extend radially outward from the hub 301 as far as possible without risking an overly small tip gap G (see FIG. 3C). Flow rate can be improved by enabling the blades 303 to extend radially outward to a greater extent in the operational configuration than in the deployed configuration.

It should be appreciated that the various parameters described herein may be selected to increase flow rate, even while reducing the rotational speed of the impeller. For example, even at relatively low impeller rotational rates of 21,000 revolutions per minute (RPM) or less (e.g., rates in a range of about 18,000 RPM to about 20,000 RPM, or more particularly, in a range of about 18,500 RPM to about 19,500 RPM in some arrangements), the blades 303 can be designed to yield relatively high flow rates in a range of about 4 liters/minute (LPM) to about 5 liters/minute. Conventional percutaneous rotary blood pumps have been found to deliver less than ideal flow rates even at rotational speeds in excess of 40,000 RPM. It should be appreciated that higher impeller rotational rates may be undesirable in some aspects, because the high rate of rotation, e.g., higher RPMs, lead to higher shear rates that generally increase hemolysis and lead to undesirable patient outcomes. By reducing the impeller rotational rate while maintaining or increasing flow rate, the pump in accordance with aspects of the invention can reduce the risk of hemolysis while significantly improving patient outcomes over conventional designs.

Furthermore, to enable percutaneous insertion of the operative device of the pump into the patient's vascular system, the impellers 300-300J disclosed herein in FIGS. 5A-11 may also include a ramped surface at a rearward or proximal end of the blade. As explained herein (see, e.g., FIG. 12), when the external sleeve is urged against the housing 202 (e.g., cannula), the external sleeve can press against the housing 202 and the ramped surface of the impeller to collapse the impeller and blades into the stored configuration. For example, the ramped surface can be used to store the blades and impeller after assembly of the pump for packaging purposes and/or after performing a heart pumping procedure for withdrawal of the pump from the anatomy.

The impellers disclosed herein may be formed of any suitable material and by any suitable process. For example, in preferred embodiments, the impeller is formed from a flexible material, e.g., an elastic material such as a polymer. Any suitable polymer can be used. In some embodiments, for example, Hapflex 598, Hapflex 798, or Steralloy or Thoralon may be used in various portions of the impeller body. In some arrangements, the impeller body can be molded to form a unitary body.

Various Impeller Designs

Turning to FIGS. 5A-5F, one embodiment of the impeller 300 is presented. It should be appreciated that FIGS. 5A-5F illustrate the same impeller 300, only showing different views and impeller parameters for ease of illustration. One or more blades 303 can extend from the hub 301, such that a fixed end of the blades 303 is integrally formed with or coupled to the hub 301. The blades 303 can also have a free end located at the tip of the blades 303. As used herein, therefore, it should be appreciated that the blades 303 can have a fixed end coupled to the hub 301 (e.g., at a blade root) and a free end at a tip of the blade 303. In the illustrated embodiments, the hub 301 and blades 303 form a single unitary, or monolithic, body. However, it should be appreciated that in other embodiments, the hub 301 and blades 303 may be formed from separate components or materials. In various implementations, the impeller 300 can include one or more blade rows extending along the hub 301.

Figure 5A:
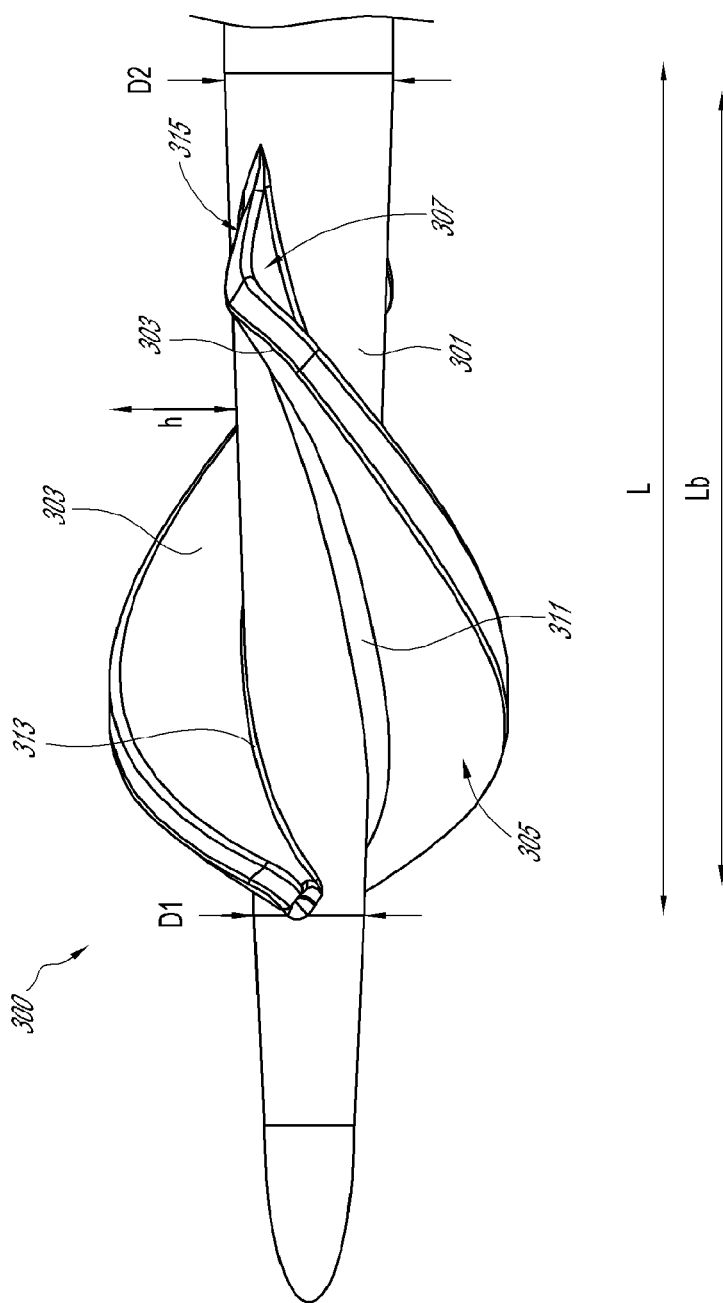
FIGS. 5A-5F are three-dimensional (3D) perspective views of an impeller according to one embodiment.

FIGS. 5A-5F illustrate the impeller 300 having one blade row and two blades 303. The hub 301 can have a first diameter $D_1$ at a distal end portion of the impeller 300 (e.g., near a leading edge of the blade(s) 303) and a second diameter $D_2$ at a proximal end portion of the impeller 300 (e.g., near a trailing edge of the blade(s) 303). As used herein and as shown in FIG. 5A, for example, a distal end portion of the impeller 300 may be disposed nearer the distal end of the catheter pump, while a proximal end portion of the impeller 300 may be disposed nearer the motor and the insertion site. As explained below, in some implementations, $D_1$ can be less than $D_2$. The hub 301 can also have a length L, and the blades 303 can have a height h, which can be the distance between the hub and the free end of the blades. Further, each blade 303 can have a blade length $L_b$, which may or may not be the same as the hub length L. As shown in FIG. 5A, the height h may be measured from the hub 301 to the free end of a middle portion of the blades 303 when the impeller is in a deployed or relaxed configuration. The height h may vary along the length of the blades 303, e.g., increasing proximally from a forward or distal end of the blades 303 to a maximum in a middle portion of the blades and decreasing from the middle portion to a rearward or proximal portion of the blades. Furthermore, as explained above, when the impeller 300 rotates and is in an operational configuration, the operational height $h_o$ may be larger than the blade height h in the deployed or relaxed configuration, which is illustrated in FIGS. 5A-5F.

Figure 5B:
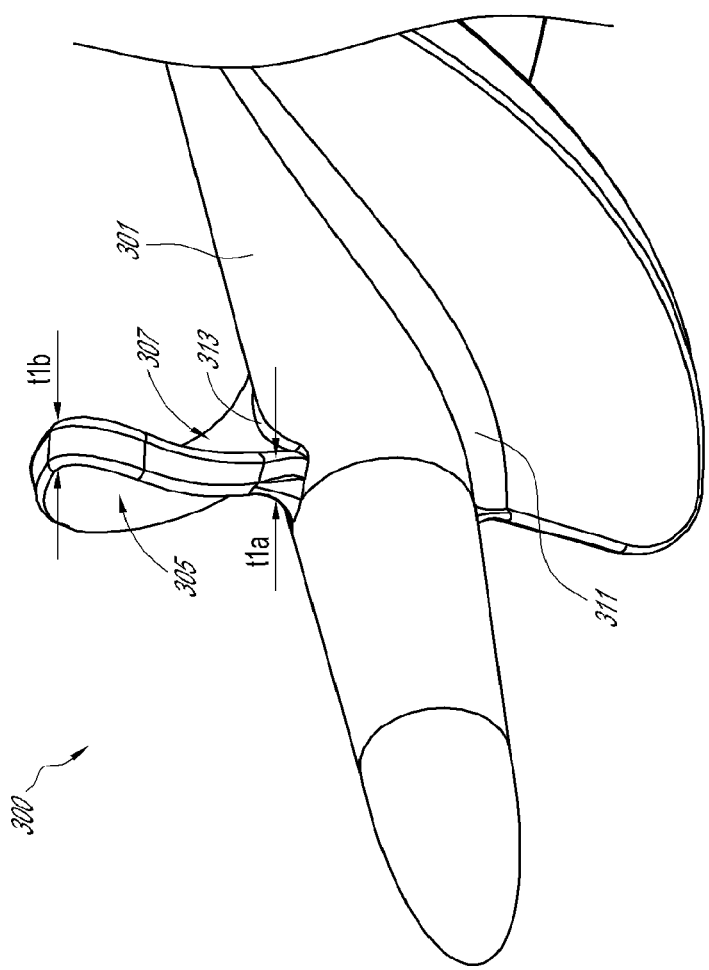
Figure 5C:
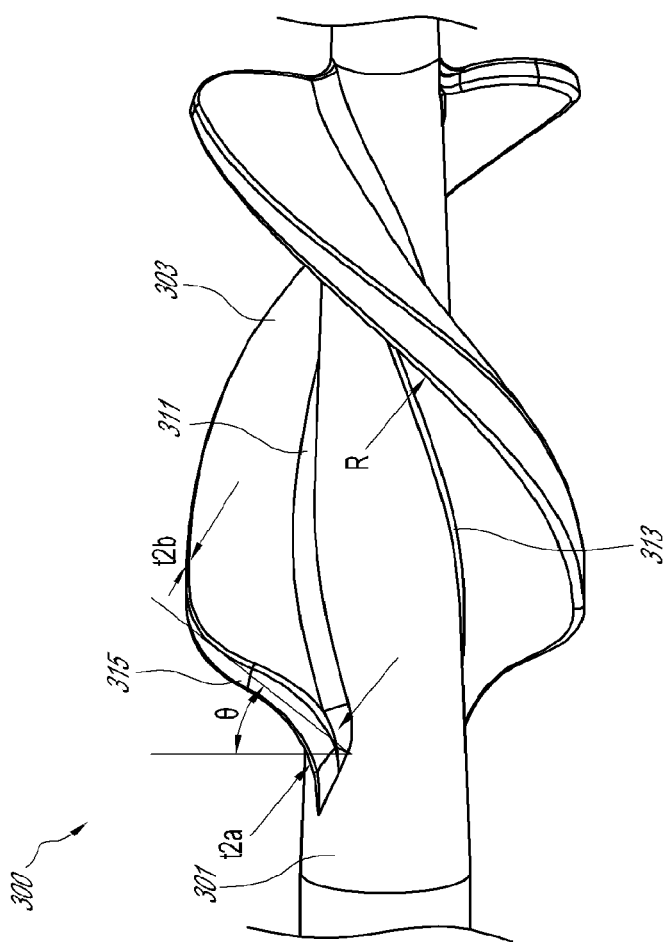

Furthermore, each blade 303 can include a suction side 305 and a pressure side 307. In general, fluid can flow from the suction side 305 of the blade 303 toward the pressure side 307 of the blade 303, e.g., from the distal end portion of the impeller 300 to the proximal end portion of the impeller 300. The pressure side 307 can be include a curved, concave surface having a predetermined radius of curvature R, as best seen in FIG. 5C, and as explained above. For example, in FIGS. 5A-5F, the illustrated radius of curvature R corresponds to a relaxed or deployed radius of curvature $R_D$. As explained above, when the impeller 300 rotates, the impeller may be in an operational configuration having an operational radius of curvature $R_o$ that may be larger than the deployed radius of curvature $R_D$. Indeed, in some embodiments, the blades 303 may substantially flatten and elongate radially such that there is little curvature. The elongated blades 303 in the operational configuration may enable for increased flow rate through the pump.

Moreover, each blade 303 can have a thickness designed to improve impeller performance. As shown in FIG. 5B, the leading edge or distal end portion of the blade 303 can have a first thickness $t_{1a}$ at the fixed end of the blade 303, where the blade 303 joins the hub 301, and a second thickness $t_{1b}$ at the free end of the blade 303. Similarly, in FIG. 5C, the trailing edge of the blade 303 can also have a first thickness $t_{2a}$ at the fixed end of the blade 303 and a second thickness $t_{2b}$ at the free end of the blade 303. Example parameters for various blades in FIGS. 5A-11 will be disclosed in the description below and in Tables 1 and 2.

Each blade 303 can wrap around the hub 301 by a desired wrapping angle. The wrapping angle can be measured along the circumference of the hub 301. As shown in the illustrated embodiments, each blade 303 can separately track a helical pattern along the surface of the hub 301 as the blade 303 wraps around the hub 301 along the length L of the hub. Table 2 and the disclosure below illustrate example wrapping angles for blades 303 in various embodiments. The blades can wrap around the hub any suitable number of turns or fractions thereof. Further, a first fillet 311 can be formed at the fixed end of each blade on the suction side 305, and a second fillet 313 can be formed at the fixed end of each blade 303 on the pressure side 307. As shown each fillet 311, 313 can follow the fixed end of each blade 303 as it wraps around the hub 301. As explained below, the first fillet 311 can be sized and shaped to provide support to the blade 303 as the impeller 300 rotates. The second fillet 313 can be sized and shaped to assist in folding or compressing the blade 303 into the stored configuration.

Figure 5D:
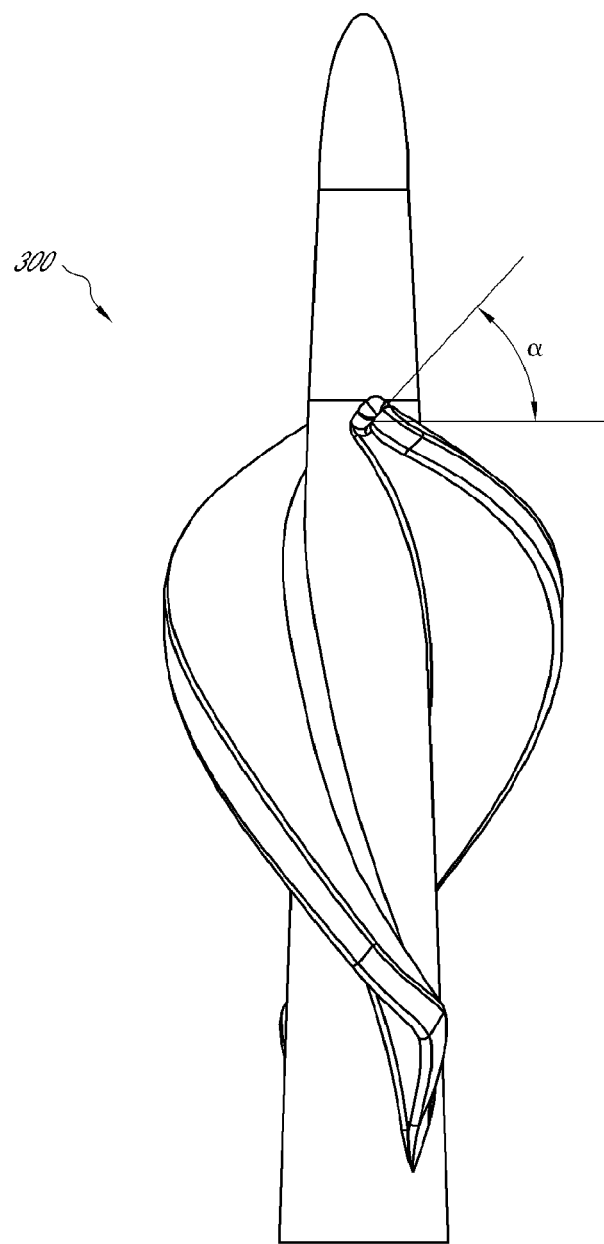
Figure 5E:
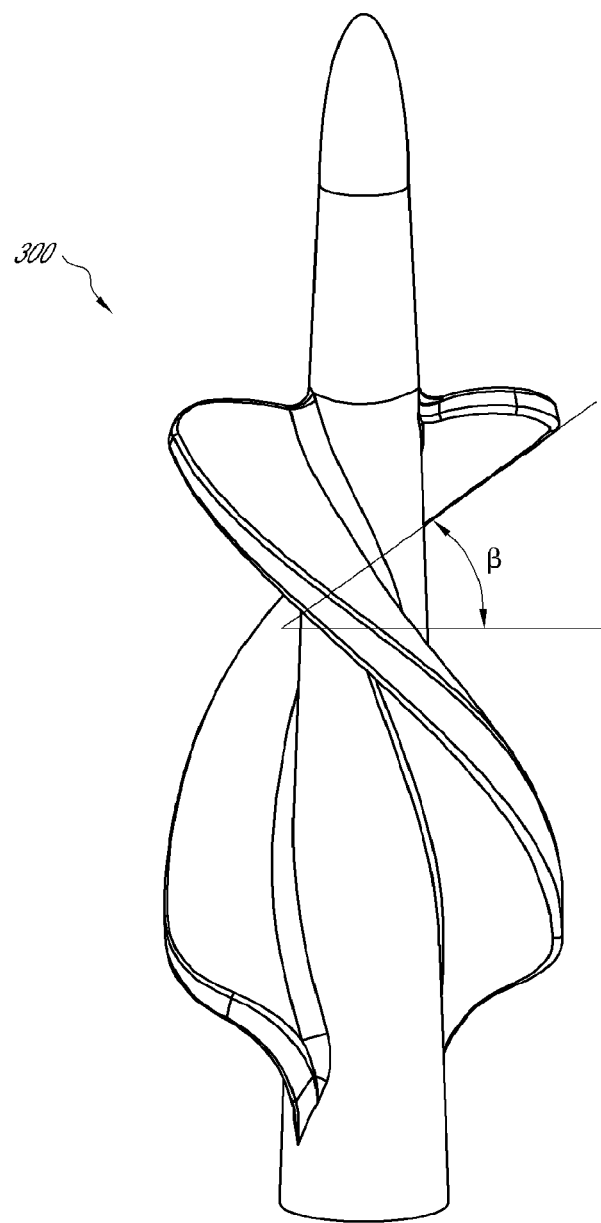
Figure 5F:
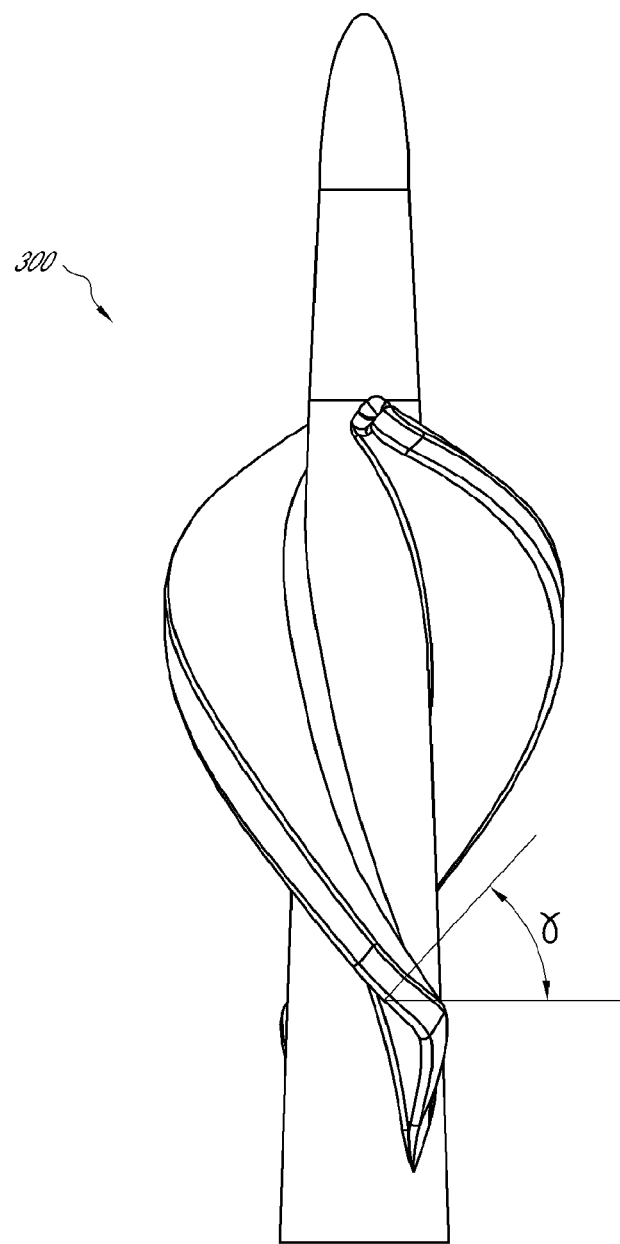

In addition, each blade 303 can form various blade angles $\alpha$, $\beta$, and $\gamma$. As shown in FIGS. 5D-F, the blade angles $\alpha$ (referred to herein as an "attack angle $\alpha$" or a "distal blade angle $\alpha$"), $\beta$ (referred to herein as a "middle blade angle $\beta$"), and $\gamma$ (referred to herein as a "proximal blade angle $\gamma$") measure the angles between a blade centerline at various portions of the blade and a plane that is perpendicular to the hub 301. For example, the attack angle $\alpha$ can measure the angle between a plane formed perpendicular to the blade near the distal portion of the blade (e.g., distally along the impeller hub in FIG. 5D) and a plane formed perpendicular to the hub 301. The attack angle $\alpha$ can range between about 30 degrees and about 60 degrees. In some implementations, $\alpha$ can range between about 40 degrees and about 55 degrees. In the implementation of FIG. 5D, for example, $\alpha$ can be in a range of about 48 degrees and about 52 degrees, e.g., about 50 degrees. The middle blade angle $\beta$ can measure the angle between a plane perpendicular to the blade in a middle portion of the blade and a plane perpendicular to the hub 301. In some implementations, $\beta$ can range from about 30 degrees to about 45 degrees. In the implementations of FIGS. 5A-5F and 6, for example, $\beta$ can be in a range of about 35 degrees and about 42 degrees, e.g., about 40 degrees. The proximal blade angle $\gamma$ can correspond to the angle between a plane perpendicular to the blade in a proximal portion of the blade (e.g., proximal with respect to the hub 301) and a plane perpendicular to the hub 301. In some embodiments, $\gamma$ can range between about 25 degrees and about 55 degrees. In the illustrated embodiment of FIG. 5F, $\gamma$ can be in a range of about 30 degrees and about 40 degrees, or about 35 degrees, for example. In some embodiments, the attack angle $\alpha$ can be larger than the middle blade angle $\beta$. Further, in some embodiments, the middle blade angle can be larger than the proximal blade angle $\gamma$. In some embodiments, the attack angle $\alpha$ can be larger than both the middle blade angle $\beta$ and the proximal blade angle $\gamma$. The blade angles $\alpha$, $\beta$, and $\gamma$ can be further designed using computational techniques to maintain desired flow characteristics, such as flow rate, pressure head, and rotational speed. For example, the disclosed blade angles can, in various impellers disclosed herein, enable flow rates in a range of about 4 liters/minute to about 5.5 liters/minute, when the impeller rotates at a speed below about 20,000 RPMs (e.g., in a range of about 19,000 RPMs to about 21,000 RPMs in some arrangements). By maintaining a high flow rate at relatively low rotational speeds, the disclosed impellers can achieve desirable patient outcomes while reducing the risk of hemolysis and increasing pump reliability.

Further, the trailing edge of each blade 303 can include a ramp 315 forming a ramp angle $\theta$ with the plane perpendicular to the hub 301, as best illustrated in FIG. 5C. The ramp 315 can be shaped such that when the sheath and housing 202 are urged against the ramp 315, or when the blades 303 and housing 202 are pulled proximally relative to and into the sheath, the axial force applied by the sheath can be transferred downward by the ramp 315 to assist in folding the blade 303 against the hub 301. The ramp angle $\theta$ can be configured to assist in folding the blade 303 against the hub 301. Further, the cross-sectional curvature and/or axial form of the blades can also be configured to reduce the force needed to collapse the impeller when used in conjunction with the ramp angle $\theta$. For example, the angle that the blades twist around the hub may be configured to direct axial forces applied by the sheath to fold the blades against the hub 301. The radius of curvature R of the blades 303 can also be selected to enable the blades 303 to conform closely to the hub 301, as explained above.

Figure 6:
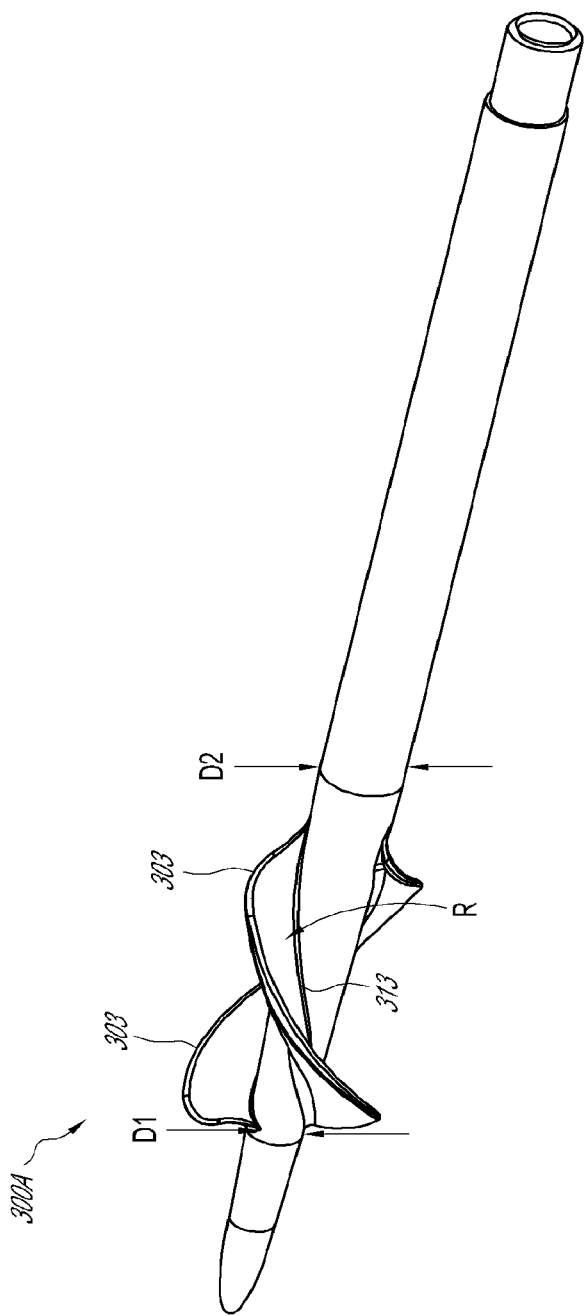
FIG. 6 is a 3D perspective view of an impeller according to another embodiment.
Figure 7:
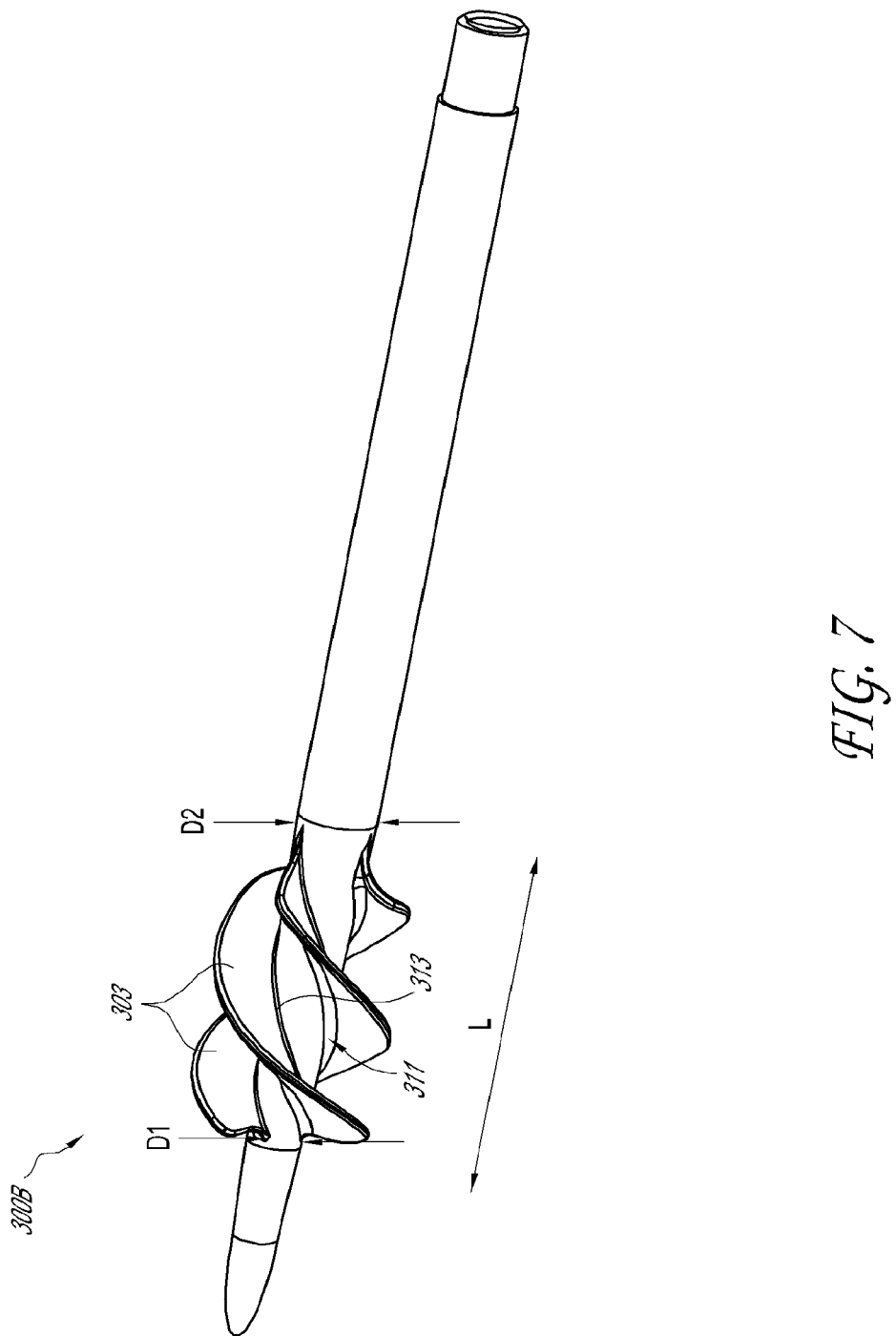
FIG. 7 is a 3D perspective view of an impeller according to yet another embodiment.
Figure 8:
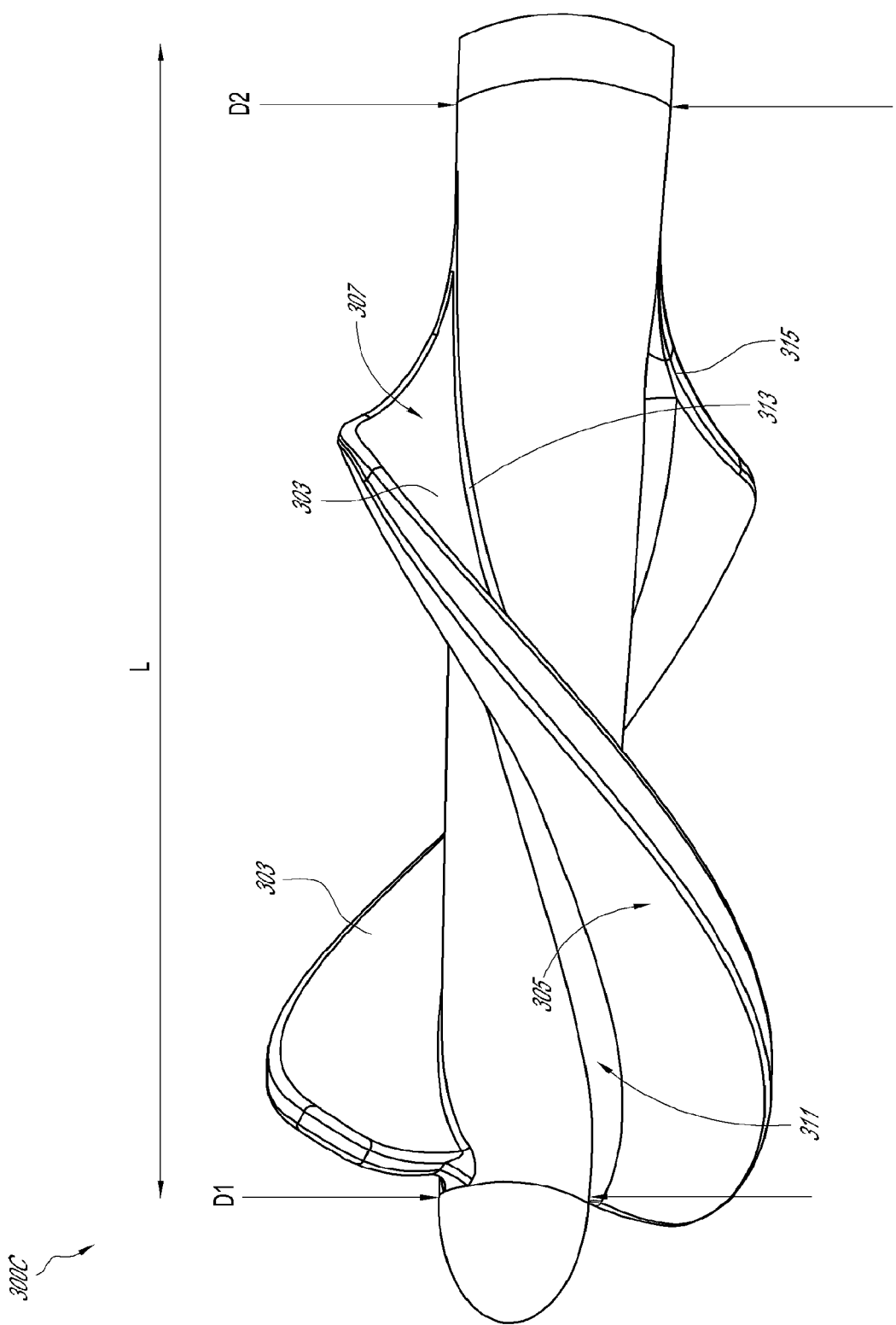
FIG. 8 is a side view of an impeller according to another embodiment.
Figure 9E:
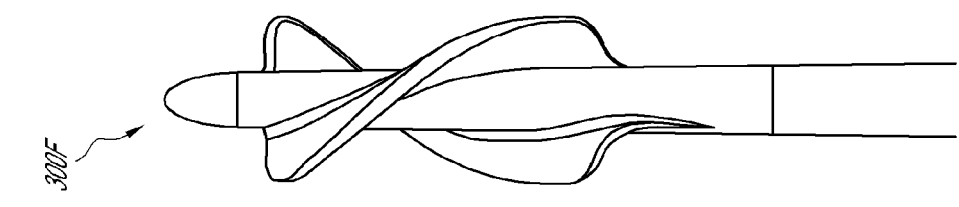
FIGS. 9A-9E are side views of impellers according to various embodiments.
Figure 9D:
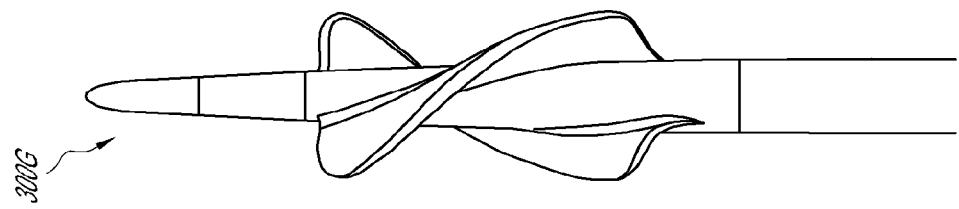
Figure 9C:
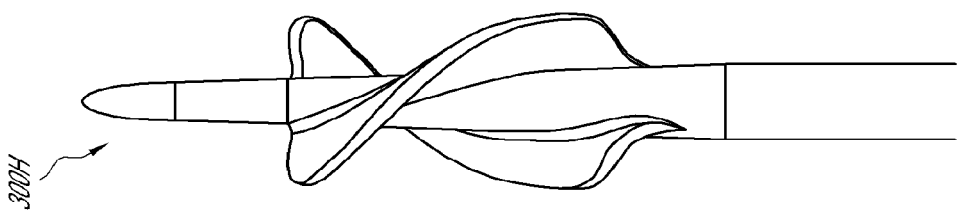
Figure 9B:
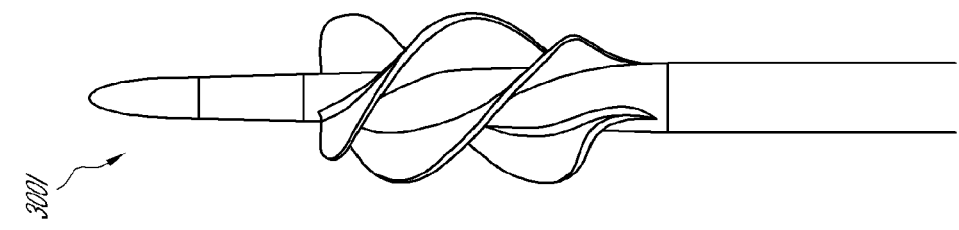
Figure 9A:
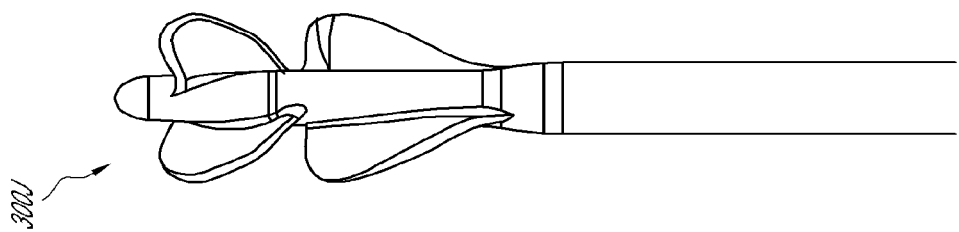
Figure 10A:
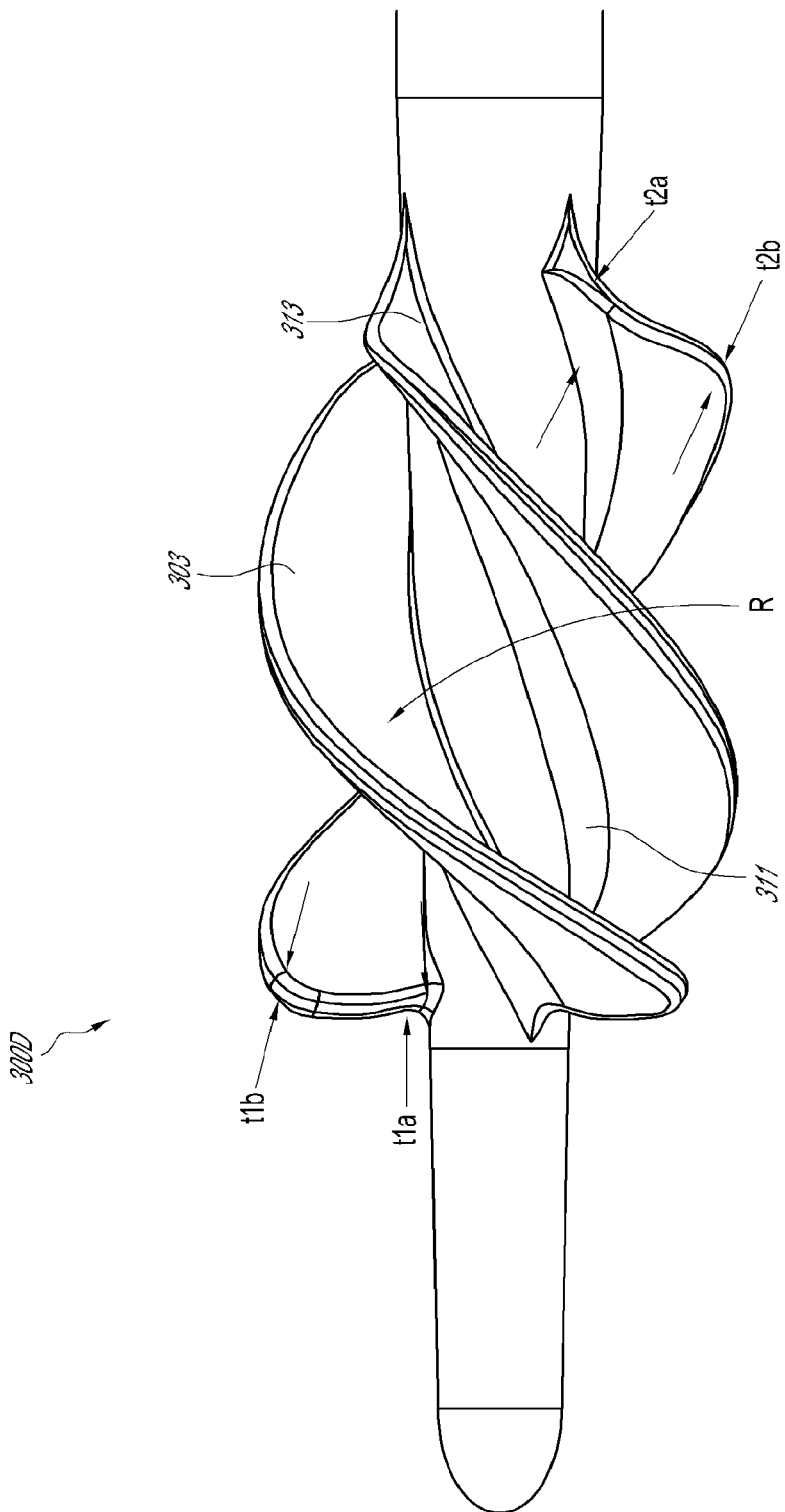
FIG. 10A is a side view of an impeller according to yet another embodiment.
Figure 10B:
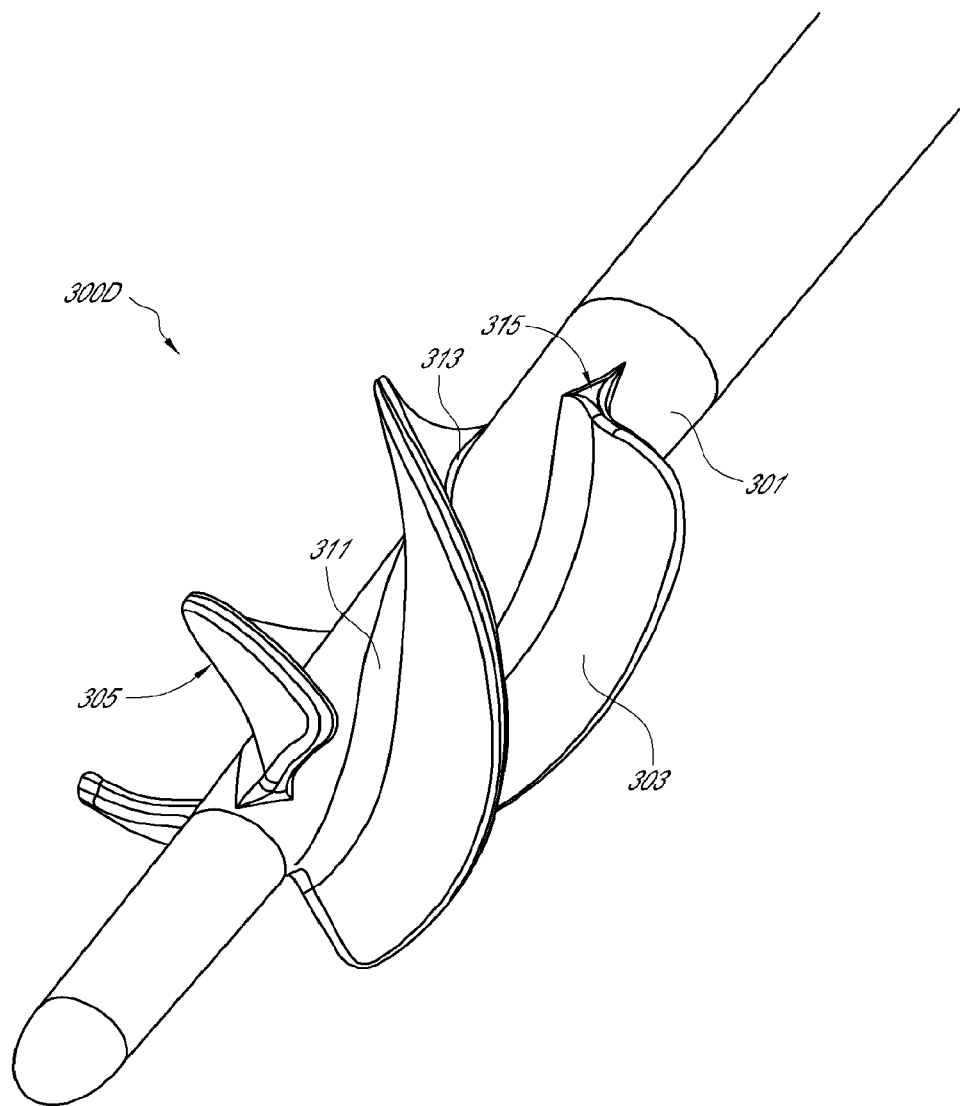
FIG. 10B is a 3D perspective view of the impeller of FIG. 10A.
Figure 11:
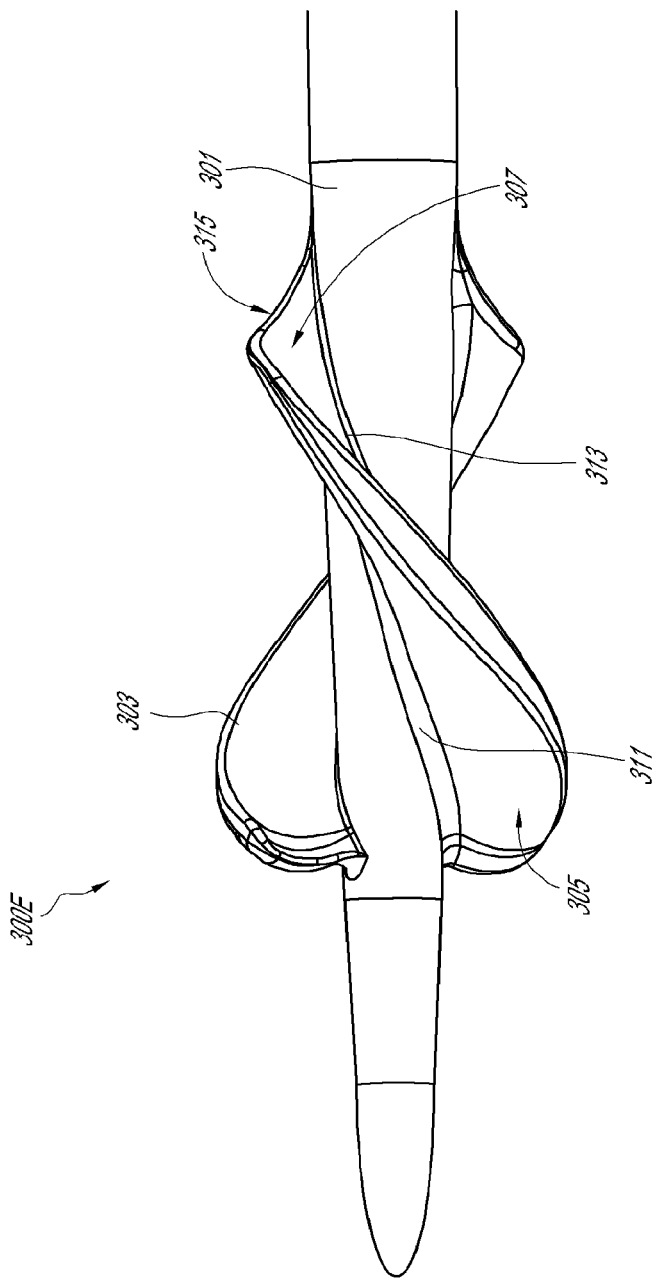
FIG. 11 is a side view of an impeller according to another embodiment.

Turning to FIGS. 6-11, other embodiments of the impeller 300 are illustrated. Reference numerals in FIGS. 6-11 generally represent components similar to those of FIGS. 5A-5F. In addition, it should be appreciated that the parameters and angles described above with reference to FIGS. 5A-5F are also present in the impellers disclosed in FIGS. 6-11, even where such parameters or angles are not specifically referenced for ease of illustration. For example, FIG. 6 illustrates an impeller 300A having two blades 303 in one blade row. On the other hand, FIG. 7 illustrates an impeller 300B having three blades 303 in a single blade row. FIG. 8 illustrates another example of an impeller 300C having two blades 303 in one blade row. FIGS. 9A-9C illustrate three impellers 300F-300H, respectively, each having two blades in one row. FIG. 9D illustrates an impeller 300I having three blades in one row. By contrast, FIG. 9E shows an impeller 300J having four blades total, with two blade rows, each blade row having two blades. FIGS. 10A-10B illustrate yet another impeller 300D having three blades 303 in a single row, while FIG. 11 shows an impeller 300E having two blades 303 in a single row. Tables 1 and 2 include various properties for the impellers 300 shown in the embodiments of FIGS. 5A-5C and 6-11. The impellers 300-300J disclosed herein may have different values for the various parameters and characteristics disclosed herein, and some of the impellers may have improved performance relative to other of the disclosed impellers.

The impellers 300 illustrated in the disclosed embodiments may have other features. For example, for impellers with multiple blade rows, the blade(s) in one row may be angularly clocked relative to the blade(s) in another row. It should be appreciated that the blades may be configured in any suitable shape or may be wrapped around the impeller hub in any manner suitable for operation in a catheter pump system.

Impeller Parameters

As explained above, various impeller parameters can be important in increasing flow rate while ensuring that the pump operates safely within the subject. Further, various properties and parameters of the disclosed impellers 300-300J of FIGS. 5A-11 may enable the impellers to more easily collapse into the stored configuration.

Hub Diameter and Length

One impeller parameter is the size of the hub, e.g., the diameter and/or the length of the hub. As illustrated in FIGS. 5A-11, the hub can be tapered in various embodiments, such that the distal end portion of the hub has a first diameter, $D_1$, and the proximal end portion of the hub has a second diameter, $D_2$. The first and second diameters, $D_1$ and $D_2$ can determine the spacing between the wall W of the housing 202 and the hub 301. Since the housing 202 effectively bounds the area through which blood can flow, the spacing between the hub 301 and the housing wall W may determine the maximum flow rate through the pump. For example, if the hub 301 has a relatively small diameter, then the flow area between the inner wall W of the housing 202 and the hub 301 may be larger than in embodiments with a larger hub diameter. Because the flow area is larger, depending on other impeller parameters, the flow rate through the pump may advantageously be increased.

One of skill in the art will appreciate from the disclosure herein that the impeller parameters may be varied in accordance with the invention. The hub diameter can vary. In some embodiments, $D_1$ can range between about 0.06 inches and about 0.11 inches. $D_2$ can range between about 0.1 inches and about 0.15 inches. For example, in the impeller shown in FIGS. 5A-5F, $D_1$ can be about 0.081 inches, and $D_2$ can be about 0.125 inches. In the implementation of FIGS. 10A and 10B, $D_1$ can be in a range of about 0.08 inches and about 0.09 inches (e.g., about 0.0836 inches in some arrangements), and $D_2$ can be in a range of about 0.12 inches and about 0.13 inches (e.g., about 0.125 inches in some arrangements).

Moreover, the length, $L_b$, of each blade can be designed in various embodiments to achieve a desired flow rate and pressure head. In general, longer blades can have higher flow rates and pressure heads. Without being limited by theory, it is believed that longer blades can support more blade material and surface area to propel the blood through the cannula. Thus, both the length of the blades and the first and second diameters $D_1$ and $D_2$ can be varied to achieve optimal flow rates. For example, $D_1$ can be made relatively small while $L_b$ can be made relatively long to increase flow rate.

Blade Height

Another impeller parameter is the height h of the blades of the impeller in the deployed, or relaxed, configuration. The height h of the blades can be varied to achieve a stable flow field and to reduce turbulence, while ensuring adequate flow rate. For example, in some embodiments, the blade can be formed to have a height h large enough to induce adequate flow through the cannula. However, because the blades are preferably flexible so that they can fold against the hub in the stored configuration, rotation of the impeller may also cause the blades to flex radially outward due to centrifugal forces. As explained above with respect to FIGS. 3A-3C, the tip gap G between the wall W of the housing 202 and the free ends of the blades can be quite small. If the blades 303 flex outwardly by a substantial amount when the impeller 300 rotates, then the distal ends of the blades 303 may impact the housing wall W, which can damage blood cells passing by. Thus, the height h may also be formed to be sufficiently small such that, upon rotation of the impeller 300, deformation of the blades 300 still maintains adequate tip gap G.

On the other hand, as explained above, the height h of the blades 303 in the deployed configuration can be selected such that when the impeller rotates, the tip or free end of the blades 303 can extend or elongate to an operational height $h_o$, which extends further radially than when in the deployed configuration, in order to increase flow rate. Thus, as explained herein, the height h and the radius of curvature $R_D$ of the blades 303 in the deployed configuration can be selected to both increase flow rate while reducing the risk of hemolysis caused by inadequate tip gap G.

In various implementations, the height of the blades near the middle of the impeller hub can range between about 0.06 inches and about 0.15 inches, for example, in a range of about 0.09 inches to about 0.11 inches. Of course, the height of the blades can be designed in conjunction with the design of the hub diameters and length, and with the radius of curvature R. As an example, for the impeller in FIGS. 5A-5C, the height h of the blade near the middle of the impeller hub can be in a range of about 0.09 inches and about 0.1 inches (e.g., about 0.0995 inches in some arrangements). In the impeller of FIGS. 10A-10B, the height h of the blade can be in a range of about 0.1 inches and about 0.11 inches (e.g., about 0.107 inches in some arrangements). Other example blade heights may be seen in Table 1.

Number of Blades

As mentioned above, impellers 300 can have any suitable number of blades 303. In general, in impellers with more blades 303, the flow rate of blood flowing through the cannula or housing 202 can be advantageously increased while reducing the required angular velocity of the drive shaft. Thus, absent other constraints, it can be advantageous to use as many blades as possible to maximize flow rate. However, because the impellers disclosed herein can be configured to fold against the hub 301 in the stored configuration for insertion into a patient's vasculature, using too many blades 303 can increase the overall volume of the impeller in the stored configuration. If the thickness of the impeller 300 in the stored configuration exceeds the diameter of the sheath or sleeve (or the diameter of the patient's artery or vein), then the impeller 300 may not collapse into the sheath for storing.

Moreover, increasing the number of blades 303 accordingly increases the number of shear regions at the free end of the blades 303. As the impeller 300 rotates, the free ends of the blades 303 induce shear stresses on the blood passing by the blades 303. In particular, the tip or free edge of the blades 303 can induce significant shear stresses. By increasing the overall number of blades 303, the number of regions with high shear stresses are accordingly increased, which can disadvantageously cause an increased risk of hemolysis in some situations. Thus, the number of blades can be selected such that there is adequate flow through the pump, while ensuring that the impeller 300 can still be stored within the sheath and that the blades 303 do not induce excessive shear stresses. In various arrangements, for example, an impeller having three blades (such as the impellers shown in FIGS. 7, 9D, and 10A-10B) can achieve an appropriate balance between increased flow rate and reduced risk of hemolysis.

Radius of Curvature

Yet another design parameter for the impeller is the radius of curvature, R, of the blades 303 on the pressure side 307 of the blades, as explained in detail above. As shown in FIGS. 5A-11, the illustrated impellers 300-300J are in the deployed configuration, such that the illustrated R corresponds to the deployed radius of curvature $R_D$. The radius of curvature R can be designed to minimize turbulence, while increasing flow rate. Turbulence can disadvantageously dissipate energy as the impeller rotates, which can reduce the flow rate. In general, higher curvature on the pressure side 307 of the blades 303 can increase turbulence. Moreover, the radius of curvature R can be designed to conform to the hub 301 such that, when the impeller is compressed by the sheath or sleeve, the curved pressure side 307 of the blade 303 conforms to the curvature of the hub 301 when the blades 303 are folded against the hub. Thus, the radius of curvature R of the blades can be designed to both reduce turbulent flow and to assist in folding the blades against the hub to ensure that the impeller 300 fits within the sheath in the stored configuration.

In addition, as explained above, when the impeller rotates and is in the operational configuration, the free end of the blades 303 may extend radially outward such that the radius of curvature in the operational configuration, $R_o$, may be higher than the radius of curvature in the operational configuration, $R_D$, which is illustrated as R in FIGS. 5A-11. Indeed, the straightening and elongation of the blades 303 in the operational configuration may advantageously increase flow rate through the pump system.

The radius of curvature can range between about 0.06 inches and about 0.155 inches in various embodiments. In some embodiments, the radius of curvature can range between about 0.09 inches and about 0.14 inches. For example, in the implementation of FIGS. 5A-5C, the cross-sectional radius of curvature R at the leading edge of the blades can be in a range of about 0.11 inches and about 0.13 inches (e.g., about 0.12 inches in some arrangements). By comparison, the radius of curvature R of the leading edge of the blades in the impeller 300 shown in FIGS. 10A-10B (in the deployed configuration) can be in a range of about 0.13 inches to about 0.14 inches (e.g., about 0.133 inches in some arrangements). Other curvatures may be suitable in various embodiments. Table 2 illustrates example values for the radius of curvature R of various embodiments disclosed herein, when the impellers are in the deployed configuration.

Blade Thickness

In addition, the thickness of the blades 303 can be controlled in various implementations. In general, the thickness of the blades can range between about 0.005 inches and about 0.070 inches in some embodiments, for example in a range of about 0.01 inches to about 0.03 inches. It should be appreciated that the thickness can be any suitable thickness. The thickness of the blade 303 can affect how the blade 303 collapses against the hub 301 when compressed into the stored configuration and how the blade deforms when rotating in an operational configuration. For example, thin blades can deform more easily than thicker blades. Deformable blades can be advantageous when they elongate or deform by a suitable amount to increase flow rate, as explained above. However, as explained above, if the blade 303 deforms outward by an excessive amount, then the free end of the blade can disadvantageously contact the inner wall of the housing 202 when the impeller 300 rotates. On the other hand, it can be easier to fold thin blades against the hub 301 because a smaller force can sufficiently compress the blades 303. Thus, it can be important in some arrangements to design a blade sufficiently stiff such that the blade 303 does not outwardly deform into the cannula or housing 202, while still ensuring that the blade 303 is sufficiently flexible such that it can be easily compressed into the stored configuration and such that it deforms enough to achieve desired flow rates.

In some embodiments, the thickness of each blade can vary along the height h of the blade. For example, the blades can be thinner at the root of the blade 303, e.g., near the hub 301, and thicker at the free end of the blade 303, e.g., near the wall W of the cannula housing 202. As best seen in FIGS. 5B-5C, for example, the leading edge of the blade can have a first thickness $t_{1a}$ at the fixed end of the blade 303 and a second thickness $t_{1b}$ at the free end of the blade 303. Moreover, the trailing edge of the blade 303 can have a first thickness $t_{2a}$ at the fixed end of the blade 303 and a second thickness $t_{2b}$ at the free end of the blade 303. Because the blades 303 are relatively thin near the hub 301, the blades 303 can be easily folded into the stored configuration due to their increased flexibility near the hub 301. Because the blades 303 are relatively thick at the free end (e.g., near the cannula wall W), the blades 303 may deform a suitable amount when the impeller rotates, reducing the risk that the blades 303 will contact or impact the wall W, which can accordingly reduce the risk of hemolysis, while deforming enough to achieve desirable flow rates. Moreover, in some embodiments, the thickness may vary continuously, such that there are no steps or discontinuities in the thickness of the blade. For example, even though the free end of the blades may be thicker in some embodiments, the thickness can continuously increase along the height of the blade.

As an example, the first thickness $t_{1a}$ of the leading edge of the blade in FIGS. 5A-5C can be in a range of about 0.016 inches to about 0.023 inches near the hub (e.g., about 0.02 inches at the hub in some arrangements), while the second thickness $t_{1b}$ can be in a range of about 0.022 inches to about 0.028 inches at the free end (e.g., about 0.025 inches at the free end in some arrangements). Further, at the trailing edge of the blade of FIGS. 5A-5C, the first thickness $t_{2a}$ can be in a range of about 0.016 inches to about 0.023 inches near the hub (e.g., about 0.02 inches at the hub in some arrangements), and the second thickness $t_{2b}$ can be in a range of about 0.03 inches to about 0.04 inches at the free end (e.g., about 0.035 inches at the free end in some arrangements). As another example, for the blade of FIGS. 10A-10B, the first thickness $t_{1a}$ of the leading edge can be in a range of about 0.022 inches to about 0.028 inches at the hub (e.g., about 0.025 inches near the hub in some arrangements), and the second thickness $t_{1b}$ can be in a range of about 0.022 inches to about 0.028 inches at the free end (e.g., about 0.025 inches at the free end in some arrangements). At the trailing edge of the blade of FIGS. 10A-10B, the first thickness $t_{2a}$ can be in a range of about 0.016 inches to about 0.023 inches at the hub (e.g., about 0.02 inches in some arrangements), and the second thickness $t_{2b}$ can be in a range of about 0.016 inches to about 0.023 inches at the free end (e.g., about 0.02 inches in some arrangements).

Fillets at Root of Blades

As explained above, a first fillet 311 can extend along the suction side 305 of each blade 303 at the proximal end of the blade 303 (e.g., at the root of the blade), and a second fillet 313 can extend along the pressure side 307 of each blade at the proximal end of the blade 303. In general the first fillet 311 can have a larger radius than the second fillet 313. The larger fillet 311 can be configured to apply a restoring force when the impeller 300 rotates in the operational configuration. As the impeller 300 rotates, the blades 303 may tend to deform in the distal direction in some situations (e.g., toward the distal portion of the hub 301). By forming the fillet 311 at the suction side 305 of the blade, the curvature of the fillet can advantageously apply a restoring force to reduce the amount of deformation and to support the blade.

By contrast, the second fillet 313 formed on the pressure side 307 of the blade 303 can have a smaller radius than the first fillet 311. The second fillet 313 can be configured to enhance the folding of the blade against the impeller when the blades 303 are urged into the stored configuration.

The radius r of each fillet can be any suitable value. For example, the radius $r_1$ of the first fillet 311 can range between about 0.006 inches and about 0.035 inches. The radius $r_2$ of the second fillet 313 can range between about 0.001 inches and about 0.010 inches. Other fillet radiuses may be suitable. For the implementation of FIGS. 5A-5C, for example, the radius $r_1$ of the first fillet 311 can be about 0.015 inches, and the radius $r_2$ of the second fillet 313 can be about 0.005 inches. By contrast, for the impeller shown in FIGS. 10A-10B, the first fillet 311 can have a radius $r_1$ of about 0.025 inches, and the second fillet 313 can have a radius $r_2$ of about 0.005 inches.

Wrapping Angle

In some implementations, the wrapping angle of each blade can be designed to improve pump performance and to enhance folding of the impeller into the stored configuration. In general, the blades can wrap around the hub at any suitable angle. It has been found that wrapping angles of between about 150 degrees and about 220 degrees can be suitable for folding the blades into the stored configuration. Further, wrapping angles of between about 180 degrees and about 200 degrees can be particularly suitable for folding the blades into the stored configuration.

Ramping Surface

Figure 12:
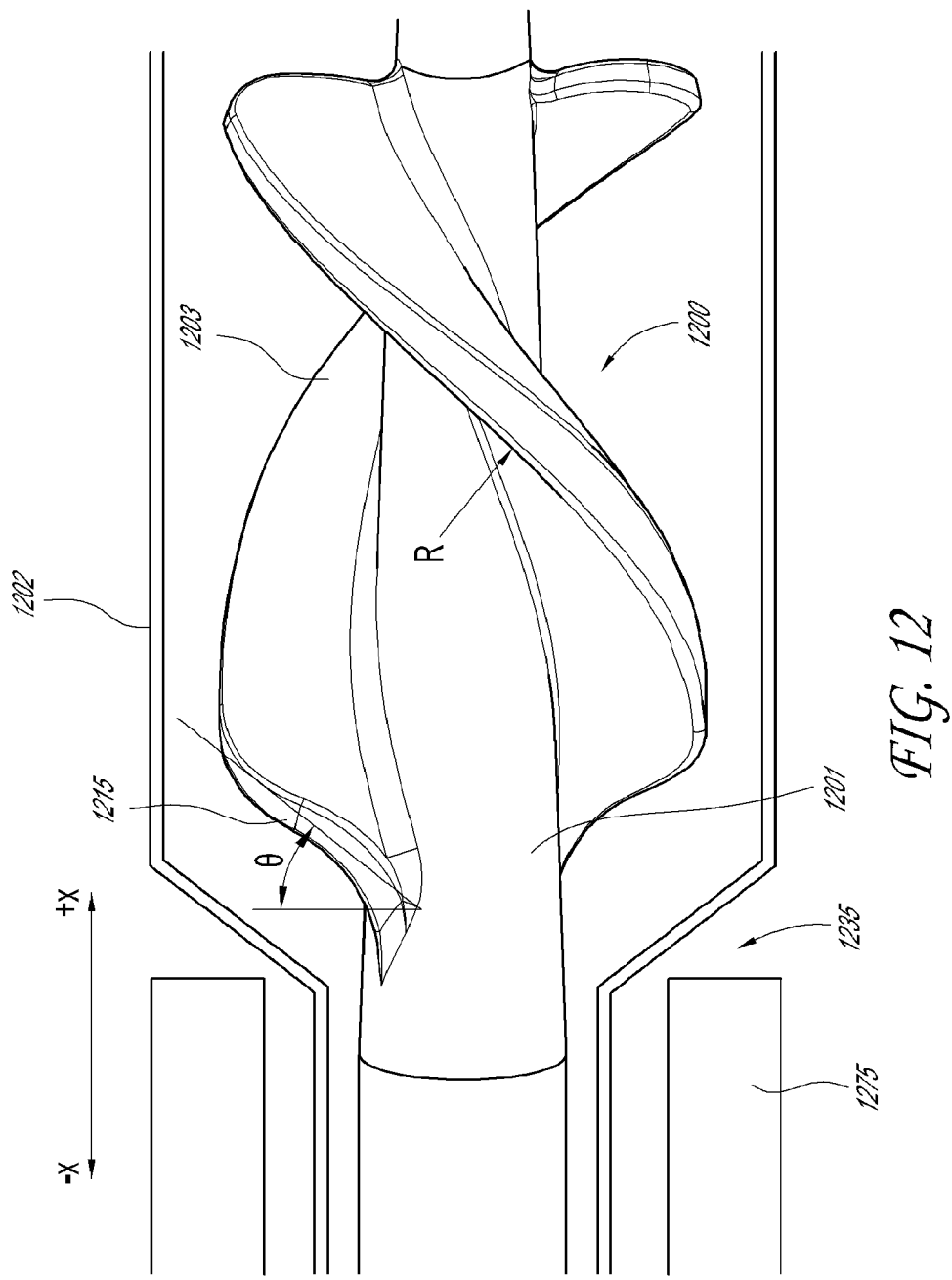
FIG. 12 is a schematic, side cross-sectional view of an impeller having a hub and one or more blades disposed within a housing.

Furthermore, as explained above, the trailing edge or the proximal end of each blade can include a ramp or chamfer formed at an angle θ with a plane perpendicular to the hub 301, as illustrated above in, e.g., FIG. 5C. FIG. 12 is a schematic, side cross-sectional view of an impeller 1200 having a hub 1201 and one or more blades 1203 disposed within a housing 1202, similar to the housing 202 described above. As shown in FIG. 12, the impeller 1200 is in the expanded or deployed configuration. For example, the impeller 1200 may be in the deployed configuration before packaging and shipping to a customer. Alternatively, the impeller 1200 may be in the deployed configuration after pumping blood in a patient and before withdrawal of the pump from the vasculature. As explained above, it can be desirable to compress the impeller 1200 into the stored configuration for inserting or withdrawing the operative device of the pump from the patient. To assist in compressing the impeller 1200 into the stored configuration, the blade(s) 1203 can include a ramp 1215 forming a ramp angle θ with a plane perpendicular to the hub 1201.

An outer sheath or sleeve 1275 can be provided around an elongate body that extends between an operative device of the pump and the motor in the system. The sleeve 1275 can be used to deploy the impeller 1200 from the stored configuration to the deployed configuration and to compress the impeller 1200 from the deployed configuration back into the stored configuration. When compressing and storing the impeller 1200 and the housing 1202, for example, a user, such as a clinician, can advance the sleeve 1275 in the +x-direction, as shown in FIG. 12. When urged in the +x-direction, the sleeve 1275 can bear against a contact portion 1235 of the housing 1202. The contact portion 1235 of the housing 1202 can in turn bear against the ramp 1215. Advantageously, the ramp angle θ can be angled distally such that when the sheath or sleeve 1275 is urged over the impeller 1200 and housing 1202, the contact portion 1235 can contact the angled or ramped edge of the blades to compress the blades against the hub. The ramp angle θ can be any suitable angle. For example, in some embodiments, the ramp angle θ can be between about 30 degrees and about 50 degrees. In the implementation of FIGS. 5A-5C and 12, for example, the chamfer or ramp angle θ of the ramp 1215 can be in a range of about 40 degrees to 50 degrees (e.g., about 45 degrees in some arrangements). In the embodiment of FIGS. 10A-10B, the ramp angle θ of the trailing edge can be in a range of about 35 degrees to 45 degrees (e.g., about 40 degrees in some arrangements). Still other ramp angles θ may be suitable to assist in storing the impeller. In some embodiment, the ramp 1215 can comprise a solid, relatively stiff portion against which the housing 202 and sheath may be advanced.

Improving Patient Outcomes

As explained herein, it can be desirable to pump blood at relatively high flow rates in order to provide adequate cardiac assistance to the patient and to improve patient outcomes. It should be appreciated that, typically, higher impeller rotational speeds may increase flow rates because the impeller is driven at a higher speed. However, one potential disadvantage of high impeller speeds is that blood passing across or over the rotating components (e.g., the impeller and/or impeller shaft or hub) may be damaged by the shearing forces imparted by the relatively rotating components. Accordingly, it is generally desirable to increase flow rates for given rotational impeller speeds.

The various features disclosed herein can enable a skilled artisan to provide an impeller capable of increasing or maintaining flow rates at lower rotational impeller speeds. These improvements are not realized by mere increases in rotational speed or optimization of the impeller design. Rather, the improvements lead to a significant shift in the performance factor of the impeller, which reflect structural advantages of the disclosed impellers.

Figure 13:
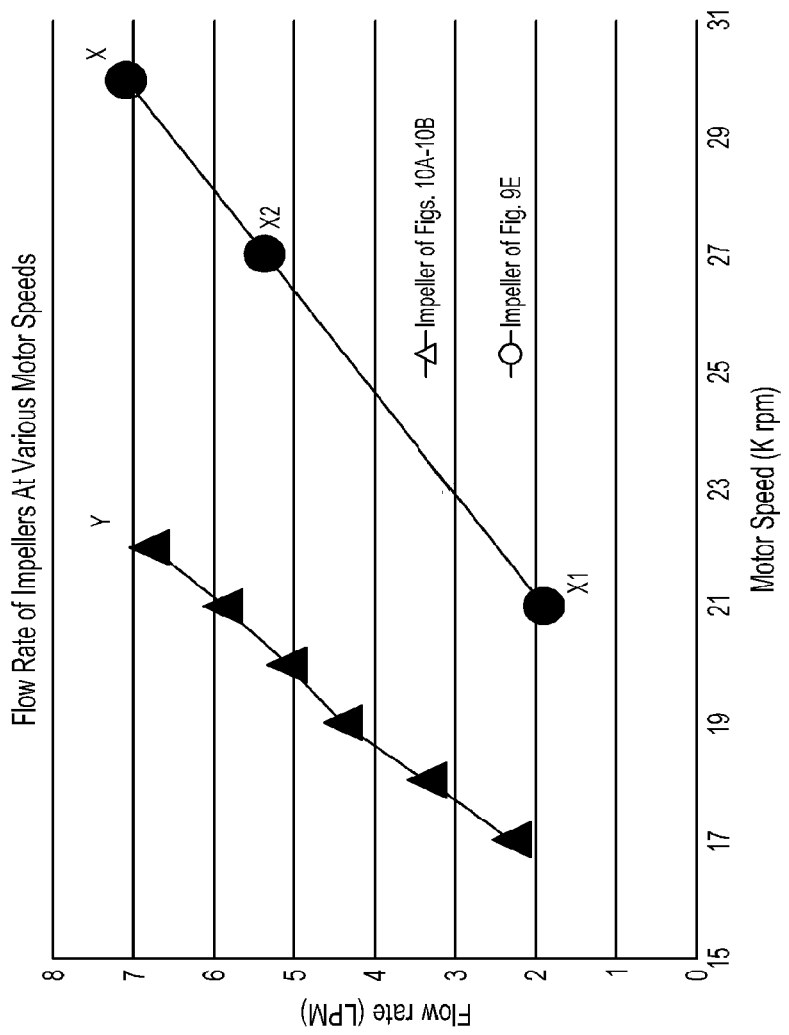
FIG. 13 is a chart plotting flow rate versus motor speed for the impellers illustrated in FIGS. 10A-10B and 9E.

FIG. 13 is a chart plotting flow rate versus motor speed for the impellers illustrated in FIGS. 10A-10B and 9E. Note that, in the illustrated chart of FIG. 13, however, that the impeller speed is the same as the motor speed, e.g., no clutch is used between the motor and impeller shaft. Thus, the plotted values in FIG. 13 represent flow rates at various impeller rotational speeds. The flow rates were measured by running the impellers on a closed mock loop on the bench with a blood analog. The back pressure (e.g., head pressure or change in pressure across the pump) was at about 62 mmHg for the impellers 300D, 300J of FIGS. 10A-10B and 9E, respectively. The results on the bench top mirror those achieved in animal investigations.

As shown in FIG. 13, the impeller 300D provides for higher flow rates at lower speeds than the impeller 300J of, e.g., FIG. 9E. For example, the impeller 300J of FIG. 9E may be capable of pumping blood at flow rates in a range of about 4.5 liters per minute (LPM) to about 5.5 LPM when the impeller is operating at speeds in a range of about 25,000 revolutions per minute (RPMs) to about 28,000 RPMs. For example, the impeller of FIG. 9E may be capable of pumping blood at a flow rate of about 5.5 LPM when the impeller is operating at speeds in a range of about 26,000 RPMs to about 28,000 RPMs.

In FIG. 13, the flow rate of the impeller 300J can be plotted along a line X, in which flow rate increases with impeller rotational speed, which is the same as motor speed in FIG. 13. With prior designs, increased flow rate can only be achieved by increasing the rotational speed to move along the line X Prior, it was expected that optimization of the impeller design can only realize minor improvements to the flow versus RPM curve. At best, the impeller could be configured to achieve minor improvements at the extremes or with a slight change in the curve X, such that the line or curve X might have a slightly higher slope.

For example, with the impeller 300J of FIG. 9E, the impeller speed at data point X1 is about 21,000 RPM, which yields a flow rate of about 1.9 LPM. With the impeller 300J of FIG. 9E, flow rate can indeed be increased to above about 5 LPM, e.g., about 5.4 LPM, at data point X2, but the impeller rotational speed required to achieve such improvements in flow rate also increases to about 27,000 RPM. Thus, even though the impeller 300J of FIG. 9E can achieve relatively high flow rates, the high flow rates come at the expense of a higher impeller speed, which, as explained above, can cause hemolysis and undesirable patient outcomes.

By contrast, the impeller 300D of FIGS. 10A-10B achieves significant and unexpected performance improvements. The exemplary impeller has been found to achieve dramatically higher flow rates at all rotational speeds. For example, the impeller 300D of FIGS. 10A-10B can achieve flow rates above 4.25 LPM, indeed even above about 5 LPM, while maintaining a low impeller speed of less than about 21,000 RPM (which, by contrast, induced a flow rate of only about 1.9 LPM in the impeller 300J of FIG. 9E). Thus, the design of the impeller 300D of FIGS. 10A-10B can advantageously achieve structural advantages relative to the impeller 300J. Indeed, the curve labeled Y in FIG. 13 illustrates the dramatic shift of the flow rate curve to the left in FIG. 13, which indicates significantly increased flow rates at lower impeller speeds relative to prior impeller designs. The exemplary impeller has also been found to have a dramatically improved head pressure versus flow rate (HQ) performance versus conventional designs.

The exemplary impeller 300D of FIGS. 10A-10B has been found to be capable of pumping blood at flow rates in a range of about 4.5 LPM to about 5.5 LPM when the impeller is operating at speeds in a range of about 19,000 RPM to about 21,000 RPM, e.g., when the impeller is operating at speeds less than about 21,000 RPMs. For instance, the impeller 300D of FIGS. 10A-10B may be capable of pumping blood at a flow rate of about 5.5 LPM when the impeller is operating at speeds in a range of about 20,000 RPMs to about 21,000 RPMs. Further, the impeller 300D of FIGS. 10A-10B may be capable of pumping blood at a flow rate of about 5 LPM when the impeller is rotating at speeds in a range of about 19,000 RPMs to about 21,000 RPMs. In some arrangements, when the impeller is operating at a speed of about 19,500 RPMs, the flow rate may be in a range of about 4.5 LPM to about 5.1 LPM.

Further, the impeller 300D of FIGS. 10A-10B is capable of pumping blood at a flow rate of at least about 3.5 LPM, and/or at least about 4.25 LPM, when the impeller is operating at speeds less than about 21,000 RPMs. For example, the impeller 300D is capable of pumping blood at a flow rate of at least 4.25 LPM when the impeller is operating at speeds in a range of about 18,500 RPM to about 22,000 RPM, for example in a range of about 18,500 RPM to about 21,000 RPM. For example, the impeller 300D is capable of pumping blood at a flow rate in a range of about 4.25 LPM to about 5.5 LPM when the impeller is operating at speeds in a range of about 18,500 RPM to about 21,000 RPM. The flow rates achieved at these impeller speeds may be achieved at a back pressure or head pressure of at least 60 mmHg, e.g., at about 62 mmHg in some embodiments. Further the impeller 300D capable of achieving the performance of FIG. 13 may also be sized and shaped to be inserted into a vascular system of a patient through a percutaneous access site having a catheter size less than about 21 FR.

The impeller 300D of FIGS. 10A-10B may therefore provide a dramatic and unexpected jump in flow rates relative to the impeller 300J of FIG. 9E. The shift in performance allows the impeller 300D to achieve a maximum flow rate far exceeding conventional and/or previous designs and at a rotational speed a mere fraction of that for which conventional pumps are designs. Thus, FIG. 13 illustrates that the impeller 300D of FIGS. 10A-10B yields improved patient outcomes and reduced hemolysis relative to the impeller 300J of FIG. 9E.

Figure 14:
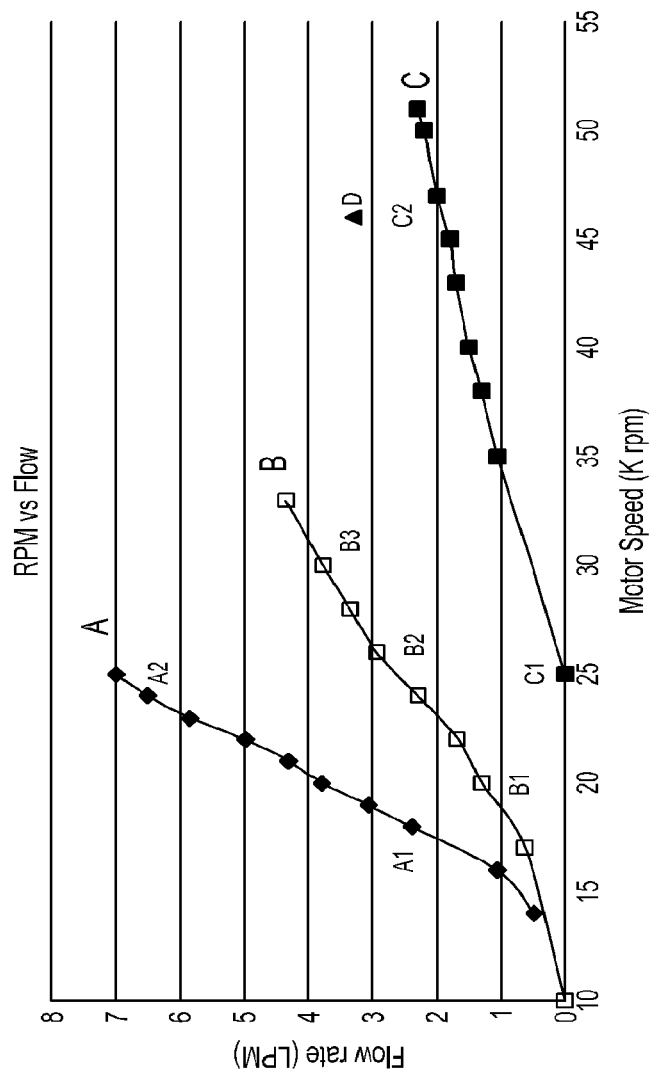
FIG. 14 is a chart plotting flow rate versus motor speed for an impeller similar to or the same as the impeller of FIGS. 10A-10B, as compared to various conventional microaxial, rotary pumps.

FIG. 14 is a chart plotting flow rate versus motor speed (e.g., impeller speed) for an impeller similar to or the same as the impeller 300D of FIGS. 10A-10B, as compared to various conventional microaxial, rotary pumps. In particular, Curve A in FIG. 14 plots flow rate versus motor speed (again, the same as impeller speed in FIG. 14) for the impeller associated with Curve A, according to test data taken using a blood analog at about 62 mmHG back pressure.

Curve B plots approximate flow rate versus motor speed for the heart pump disclosed in the article of J. Stolinski, C. Rosenbaum, Willem Flameng, and Bart Meyns, "The heart-pump interaction: effects of a microaxial blood pump," *International Journal of Artificial Organs*, vol:25 issue:11 pages:1082-8, 2002, which is incorporated by reference herein in its entirety and for all purposes. The test data from Curve B was obtained under test conditions having a back pressure of about 60 mmHg.

Curve C plots approximate flow rate versus motor speed for the heart pump disclosed in the article of David M. Weber, Daniel H. Raess, Jose P. S. Henriques, and Thorsten Siess, "Principles of Impella Cardiac Support," *Supplement to Cardiac Interventions Today*, August/September 2009, which is incorporated by reference herein in its entirety and for all purposes. The test data from Curve C was obtained under test conditions having a back pressure of about 60 mmHg.

Data point D plots approximate flow rate versus motor speed for the heart pump disclosed in Federal and Drug Administration 510(k) Summary for Predicate Device IMPELLA 2.5 (K112892), prepared on Sep. 5, 2012, which is incorporated by reference herein in its entirety and for all purposes. In particular, for data point D, the disclosed pump was capable of mean flow rates of up to 3.3 LPM at pump speeds of 46,000 RPM at a 60 mmHg differential pressure.

As shown in FIG. 14, the disclosed impeller associated with Curve A can achieve higher flow rate at all impeller speeds relative to the pumps of Curves B, C, and D. The data reflected in FIG. 14 was not all collected by precisely the same methodology in a head-to-head fashion, as noted above. However, the data are shown on a single chart for the convenience of the reader and are still compelling. For example, as discussed above, the back-pressure conditions under which the Curve A data was collected (for impellers disclosed herein) was higher than that collected for the other devices. Were this test condition the same, the results would be all the more impressive. Indeed, data points A1 and A2 of Curve A, for example, provide higher flow rates at significantly lower impeller rotation rates than any of the data points along Curves B-C or at point D (e.g., data points B1, B2, B3, C1, C2). In addition, as shown in FIG. 14, the impeller of Curve A can achieve flow rates of about 7 LPM at impeller speeds of only about 25,000 RPM, as shown by Curve A. By contrast, curves B-C and data point D do not even indicate that the conventional axial pumps can achieve 7 LPM flow rates at any impeller speed. Thus, the impeller associated with Curve A of FIG. 14 can achieve higher flow rates at lower rotational speeds than conventional catheter pumps, such as microaxial, rotary pumps, (e.g., Curves B-C and data point D of FIG. 14). In addition, the disclosed impellers can also be configured to achieve higher maximum flow rates than conventional pumps.

In addition, the data of Curves B-C and data point D of FIG. 14 represent another constraint on the design of conventional rotary pumps. For example, the pump plotted on Curve B has a diameter corresponding to a catheter size of about 21 FR. Flow rates may be increased for the pump of Curve B by increasing the diameter of the pump. However, further increases in pump diameter for the device of Curve B may disadvantageously increase the pump diameter requiring more invasive techniques to position the pump. Thus, increasing flow rate by increasing pump diameter may not be a feasible or desirable alternative for catheter pumps, and/or it may not be desirable for acute heart failure where fast implantation is critically important.

By contrast, as shown in Curve A of FIG. 14, the impeller (e.g., which can be the same as or similar to the impeller 300D disclosed herein) advantageously has an insertion diameter corresponding to a catheter size of less than about 13 FR, e.g., about 12.5 FR in some embodiments, which can enable minimally-invasive insertion techniques, even at higher flow rates and lower impeller rotation rates. Thus, the disclosed impeller of Curve A can provide higher flow rates at lower impeller speeds than conventional microaxial, rotary pumps, and can maintain lower insertion diameters for minimally invasive techniques.

Indeed, the impeller of Curve A may be configured to be inserted into vascular system of a patient through a percutaneous access site having a size less than 21 FR. The impeller of Curve A (e.g., which may be similar to or the same as impeller 300D) may include one or more blades in a single row. In some embodiments, the impeller can be configured to pump blood through at least a portion of the vascular system at a flow rate of at least about 2.0 liters per minute when the impeller is rotated at a speed less than about 21,000 revolutions per minute. In some embodiments, the blades are expandable.

Blade Height-to-Hub Diameter Ratio

In some embodiments, a ratio σ of blade height (h) to hub diameter (D) can be defined. As explained above, the hub 301 can have a first diameter $D_1$ at a distal end portion of the impeller 300 (e.g., near a leading edge of the blade(s) 303) and a second diameter $D_2$ at a proximal end portion of the impeller 300 (e.g., near a trailing edge of the blade(s) 303). As used herein, the ratio σ may be defined relative to a diameter D, which, in some embodiments, may correspond to the first diameter $D_1$ or the second diameter $D_2$, or to an average of $D_1$ and $D_2$. The blade height h may be identified relative to the deployed configuration in some embodiments. As shown in FIGS. 5A-11, the height h may be defined by a maximum distance between the hub 301 and the free end of the blade(s) 303.

The ratio σ may be relatively large compared to conventional impellers. For example, as explained herein, it can be advantageous to provide for an impeller 300 having a low profile suitable, for example, for percutaneous insertion into the patient's vascular system. One way to provide a low profile impeller 300 is to reduce the volume of impeller material that is compressed within the outer sheath, e.g., the sheath within which the impeller 300 is stored during percutaneous delivery and insertion. Impellers having relatively large blade height-to-hub diameter ratios σ may allow for such compact insertion, while maintaining high flow rates. For example, larger blade heights h can allow for the use of smaller hub diameters D, and the larger blade heights h are also capable of inducing high flow rates that are advantageous for catheter pump systems. For example, in some embodiments, the blade height-to-hub diameter ratio σ can be at least about 0.95, at least about 1, at least about 1.1, and/or at least about 1.2, in various arrangements. In some embodiments, for example, the ratio σ can be in a range of about 0.7 to about 1.45 in various embodiments. In particular, the ratio σ can be in a range of about 0.7 to about 1.1 in some embodiments (such as the embodiment of FIGS. 10A-10B, for example). In addition, in some arrangements, the ratio σ can be in a range of about 0.75 to about 1. In some embodiments, the ratio σ can be in a range of about 0.9 to about 1.1.

Example Impeller Parameters

It should be appreciated that the values for the disclosed impeller parameters are illustrative only. Skilled artisans will appreciate that the blade parameters can vary according to the particular design situation. However, in particular embodiments, the blade parameters can include parameter values similar to those disclosed in Tables 1-2 below. Note that length dimensions are in inches and angles are in degrees.

TABLE 1

| FIG. Number | No. of Blades | $D_1$ (in.) | $D_2$ (in.) | h (in.) | $t_{1a}$ (in.) | $t_{1b}$ (in.) | $t_{2a}$ (in.) | $t_{2b}$ (in.) |
|---|---|---|---|---|---|---|---|---|
| 5A-5F | 2 | 0.081 | 0.125 | 0.0995 | 0.02 | 0.025 | 0.02 | 0.035 |
| 6 | 2 | 0.081 | 0.125 | 0.1 | 0.02 | 0.02 | 0.015 | 0.02 |
| 7 | 3 | 0.0844 | 0.125 | 0.1025 | 0.015 | 0.015 | 0.02 | 0.02 |
| 8 | 2 | 0.097 | 0.12 | 0.107 | 0.015 | 0.02 | 0.015 | 0.02 |
| 10A-10B | 3 | 0.0836 | 0.125 | 0.107 | 0.025 | 0.025 | 0.02 | 0.02 |
| 11 | 2 | 0.0798 | 0.125 | 0.109 | 0.03 | 0.025 | 0.015 | 0.02 |

TABLE 2

| FIG. Number | β (deg) | Wrap Angle (deg) | θ (deg) | $r_1$ (in.) | $r_2$ (in.) | R (in.) |
|---|---|---|---|---|---|---|
| 5A-5F | 40 | 210 | 45 | 0.015 | 0.005 | 0.12 |
| 6 | 40 | 210 | 45 | 0.015 | 0.005 | 0.07 |
| 7 | 40 | 270 | 46 | 0.015 | 0.005 | 0.133 |
| 8 | 40 | 200 | 40 | 0.015 | 0.005 | 0.12 |
| 10A-10B | 40 | 220 | 40 | 0.025 | 0.005 | 0.133 |
| 11 | 30 | 210 | 35 | 0.015 | 0.005 | 0.09 |

One will appreciate from the description herein that the configuration of the blades may be modified depending on the application. For example, the angle of attack of the blades may be modified to provide for mixed flow, axial flow, or a combination thereof. The exemplary blades of the illustrated figures are dimensioned and configured to improve axial flow and reduce hemolysis risk. The exemplary blades are shaped and dimensioned to achieve the desired pressure head and flow rate. In addition, the single blade row design is thought to reduce the turbulent flow between blade rows with other designs and thus may reduce hemolysis.

Although the inventions herein have been described with reference to particular embodiments, it is to be understood that these embodiments are merely illustrative of the principles and applications of the present inventions. It is therefore to be understood that numerous modifications can be made to the illustrative embodiments and that other arrangements can be devised without departing from the spirit and scope of the present inventions as defined by the appended claims. Thus, it is intended that the present application cover the modifications and variations of these embodiments and their equivalents.

What is claimed is:

1. An impeller for a catheter pump, the impeller comprising:
    a hub having a proximal end portion and a distal end portion;
    a first row of blades extending from the proximal portion of the hub, the first row of blades comprising a first plurality of circumferentially-spaced blades, wherein each blade of the first row of blades has a blade first proximal end and a blade first distal end, and wherein the hub comprises a first diameter at the blade first distal end and a second diameter at the blade first proximal end that is larger than the first diameter;
    a second row of blades extending from the distal portion of the hub, the second row of blades comprising a second plurality of circumferentially-spaced blades, wherein the first plurality of blades is circumferentially offset with respect to the second plurality of blades about a surface of the hub.

2. The impeller of claim 1, wherein the first row is positioned at the proximal end portion and the second row is positioned at the distal end portion.

3. The impeller of claim 1, wherein the first row of blades and the second row of blades each comprise at least two blades.

4. The impeller of claim 1, wherein the first row of blades and the second row of blades each comprise at least three blades.

5. The impeller of claim 1, wherein the first row of blades and the second row of blades each comprise an equal number of blades.

6. The impeller of claim 1, wherein each blade of the second row of blades has a second proximal end and second distal end, wherein a circumferential gap defined along the hub between the first distal end and the second proximal end.

7. The impeller of claim 6, wherein an axial gap is defined between the first distal end and the second proximal end along the hub.

8. The impeller of claim 6, wherein the first distal end and the second proximal end are axially aligned along the hub.

9. The impeller of claim 1, wherein each blade of the first row of blades and the second row of blades wraps helically around the hub.

10. A catheter pump comprising:
    a catheter; and
    an impeller mounted at an end of the catheter, the impeller comprising:
        a hub having a proximal end portion and a distal end portion; and
        a first row of blades extending from the proximal portion of the hub, the first row of blades comprising a first plurality of circumferentially-spaced blades, wherein each blade of the first row of blades has a blade first proximal end and a blade first distal end, and wherein the hub comprises a first diameter at the blade first distal end and a second diameter at the blade first proximal end that is larger than the first diameter;
        a second row of blades extending from the distal portion of the hub, the second row of blades comprising a second plurality of circumferentially-spaced blades, wherein the first plurality of blades is circumferentially offset with respect to the second plurality of blades about a surface of the hub.

11. The catheter pump of claim 10, wherein the first row is positioned at the proximal end portion and the second row is positioned at the distal end portion.

12. The catheter pump of claim 10, wherein the first row of blades and the second row of blades each comprise at least two blades.

13. The catheter pump of claim 10, wherein the first row of blades and the second row of blades each comprise at least three blades.

14. The catheter pump of claim 10, wherein the first row of blades and the second row of blades each comprise an equal number of blades.

15. The catheter pump of claim 10, wherein each blade of the second row of blades has a second proximal end and second distal end, wherein a circumferential gap defined along the hub between the first distal end and the second proximal end.

16. The catheter pump of claim 15, wherein an axial gap is defined between the first distal end and the second proximal end along the hub.

17. The catheter pump of claim 15, wherein the first distal end and the second proximal end are axially aligned along the hub.

18. The catheter pump of claim 10, wherein each blade of the first row of blades and the second row of blades wraps helically around the hub.

19. A method of storing an impeller within a sheath for a catheter pump, the method comprising:
    providing a hub having a proximal end portion and a distal end portion, the hub supporting at least a first row of blades and a second row of blades, wherein each of the first row of blades and the second row of blades comprises a plurality of blades, wherein the blades of the first row are circumferentially offset with respect to the blades of the second row about a surface of the hub, wherein each blade of the first row of blades has a blade first proximal end and a blade first distal end, and wherein the hub comprises a first diameter at the blade first distal end and a second diameter at the blade first proximal end that is larger than the first diameter;
    inserting the hub into the sheath; and
    collapsing the first row of blades and the second row of blades into a stored configuration such that the plurality of blades do not overlap when in a stored configuration.

* * * * *